US010625000B2

(12) United States Patent
Croizat et al.

(10) Patent No.: US 10,625,000 B2
(45) Date of Patent: Apr. 21, 2020

(54) METHODS AND DEVICES FOR CONTROLLING NEGATIVE PRESSURE AT A WOUND SITE

(71) Applicant: Paul Hartmann AG, Heidenheim (DE)

(72) Inventors: Pierre Croizat, Herbrechtingen (DE); Jürgen Hofstetter, Heldenheim (DE); James Stein, Cambridge (GB); Chris Dawber, Cambridge (GB); Mark Hsieh, Cambridge (GB)

(73) Assignee: Paul Hartmann AG, Heidenheim (DE)

( * ) Notice: Subject to any disclaimer, the term of this patent is extended or adjusted under 35 U.S.C. 154(b) by 529 days.

(21) Appl. No.: 15/390,056

(22) Filed: Dec. 23, 2016

(65) Prior Publication Data
US 2017/0189588 A1    Jul. 6, 2017

(30) Foreign Application Priority Data
Dec. 30, 2015  (EP) ..................................... 15203110

(51) Int. Cl.
*A61M 1/00*  (2006.01)
*A61M 27/00*  (2006.01)
(Continued)

(52) U.S. Cl.
CPC ........ *A61M 1/0025* (2014.02); *A61M 1/0031* (2013.01); *A61M 1/0088* (2013.01); *A61M 2205/15* (2013.01); *A61M 2205/18* (2013.01); *A61M 2205/3331* (2013.01); *A61M 2205/3337* (2013.01); *A61M 2205/3344* (2013.01);
(Continued)

(58) Field of Classification Search
CPC ......... A61M 1/00; A61M 27/00; A61F 13/00; A61F 13/02; A61K 9/22
See application file for complete search history.

(56) References Cited

U.S. PATENT DOCUMENTS 7,022,113 B2 *   4/2006   Lockwood .......... A61M 1/0031
                                                            601/6
7,862,339 B2 *   1/2011   Mulligan ............... A61M 27/00
                                                            434/268

(Continued)

FOREIGN PATENT DOCUMENTS

DE   102009038130   2/2011
DE   102009038131   2/2011

(Continued)

*Primary Examiner* — Tatyana Zalukaeva
*Assistant Examiner* — Ilya Y Treyger
(74) *Attorney, Agent, or Firm* — Dilworth & Barrese, LLP

(57) ABSTRACT

The invention relates to a method for estimating a negative pressure at a wound site during a negative pressure wound therapy. The method comprises the steps of determining a negative pressure value by means of a pressure sensor, determining a pump speed associated with the electrical pump, multiplying the pump speed by a constant to obtain a modification value, and combining said modification value with the negative pressure value determined by means of the pressure sensor to obtain a modified negative pressure value. Said modified negative pressure value corresponds to the estimated negative pressure present at the wound site. The invention further relates to a negative pressure wound therapy system adapted to execute said method of estimating a negative pressure at a wound site.

10 Claims, 16 Drawing Sheets

(51) Int. Cl.
 *A61F 13/00* (2006.01)
 *A61F 13/02* (2006.01)
 *A61K 9/22* (2006.01)

(52) U.S. Cl.
 CPC ............ *A61M 2205/3365* (2013.01); *A61M 2205/3382* (2013.01); *A61M 2205/50* (2013.01); *A61M 2205/505* (2013.01); *A61M 2205/52* (2013.01); *A61M 2205/583* (2013.01)

(56) References Cited

U.S. PATENT DOCUMENTS

| | | | |
|---|---|---|---|
| 8,540,688 | B2 | 9/2013 | Eckstein et al. |
| 8,635,921 | B2 | 1/2014 | Eckstein et al. |
| 8,657,806 | B2 | 2/2014 | Eckstein et al. |
| 8,668,677 | B2 | 3/2014 | Eckstein et al. |
| 2004/0073151 | A1 | 4/2004 | Weston |
| 2008/0281281 | A1 | 11/2008 | Meyer et al. |
| 2010/0150991 | A1* | 6/2010 | Bernstein ............... A61K 31/00 424/447 |
| 2011/0112494 | A1* | 5/2011 | Svedman ............ A61M 1/0037 604/319 |
| 2012/0289913 | A1 | 11/2012 | Eckstein et al. |
| 2016/0045647 | A1 | 2/2016 | Croizat et al. |
| 2016/0074637 | A1 | 3/2016 | Croizat et al. |

FOREIGN PATENT DOCUMENTS

| | | |
|---|---|---|
| DE | 102011075844 | 11/2012 |
| EP | 0777504 | 10/1998 |
| EP | 1095465 | 4/2008 |
| EP | 1863549 | 2/2012 |
| EP | 2464393 | 9/2015 |
| EP | 2464394 | 9/2015 |
| WO | 2008039314 | 4/2008 |
| WO | 2009047524 | 4/2009 |
| WO | 2010072349 | 7/2010 |
| WO | 2012156174 | 11/2012 |
| WO | 2014177544 | 11/2014 |
| WO | 2014177545 | 11/2014 |

* cited by examiner

Figure 2
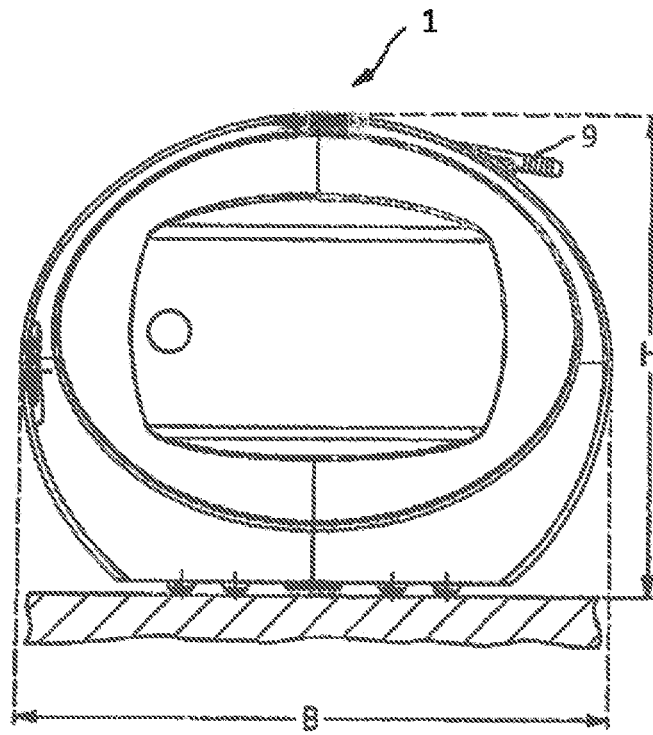
Fig. 2a
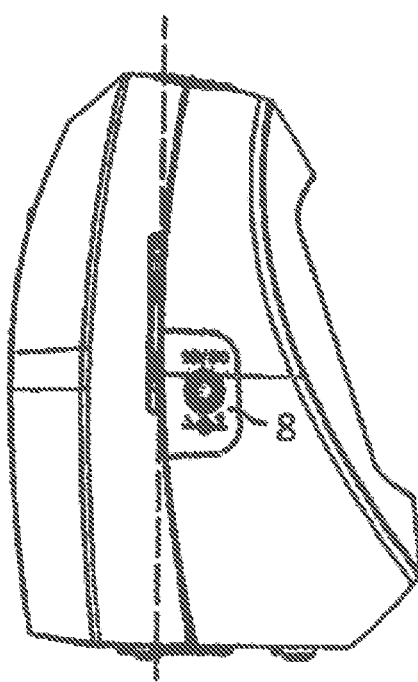
Fig. 2b

METHODS AND DEVICES FOR CONTROLLING NEGATIVE PRESSURE AT A WOUND SITE

FIELD OF THE INVENTION

The invention relates to control methods for a negative pressure wound therapy system. In particular, the invention relates to a method of estimating a negative pressure at a wound site during a negative pressure wound therapy. Moreover, the invention relates to a negative pressure wound therapy system adapted to execute the wound pressure estimation method according to the invention.

BACKGROUND

Negative pressure wound treatment devices (vacuum wound treatment devices) have been described many times, in particular, in US 2004/0073151 A1, WO 2009/047524 A2, EP 1 905 465 A1, WO 2008/039314 A2 or EP 777 504 B1 as well as in EP 1 863 549 B1, EP 2 464 394 A1, WO 2012/156174 A1 or EP 2 464 393 A1 of the assignee.

In devices of this type for negative pressure wound therapy (npwt), a suction pump (sometimes incorrectly called "vacuum pump") communicates with the wound or the wound area via a suction line, wherein a wound dressing and an air-tight cover material is provided for air-tight sealing of the wound and the wound area, such that a negative pressure can be generated in the wound region and fluids can be extracted by suction from the wound region.

The term negative pressure in connection with the present invention defines an air pressure that is lower than the ambient air pressure (atmospheric air pressure). The cover material of a wound dressing for air-tight sealing of a wound region must therefore be designed in such a fashion that it withstands the pressure difference that is established such that a negative pressure can actually be applied to and maintained in the wound region. The wound dressing and the cover material are, however, typically flexible to a certain degree. In the field of negative pressure therapy for the treatment of wounds, the negative pressure is quantitatively defined as the pressure difference between ambient air pressure and the air pressure applied below the cover material. In the field of negative pressure therapy, this pressure difference is typically at most 250 mmHg (mm mercury column) (1 mm Hg=1 Torr=133.322 Pa). This negative pressure range of up to maximally 250 mmHg has turned out to be suitable for wound healing. A preferred negative pressure range is between 10 and 150 mmHg.

For typical negative pressure treatment, the negative pressure that is applied to the wound using the device can either be kept substantially constant with time or can be varied with time, in particular in cycles which can be realized by a correspondingly designed and programmed control device for the negative pressure-generating device, in particular in dependence on further parameters.

An advantageous flexible suction line, e.g. in the form of a drainage hose, is provided for applying a negative pressure and advantageously also for extracting body fluids, the drainage hose communicating at one end with the wound area or the wound region via a so-called port in the area of the wound cover material, and at the other end communicating with a container for receiving the sucked body fluids or with the negative pressure generating device.

In addition to negative pressure wound treatment, the present invention may also be used for other applications for providing a negative pressure for medical applications, in particular, extraction of any body fluids by suction, in the field of medical incontinence management, in the field of care of stoma patients or in the field of extraction of wound exudates, if necessary, thereby using rinsing liquids and also without application of a negative pressure over considerable time periods.

In general, negative pressure wound therapy apparatuses are available as stationary or as portable devices. The before-mentioned definition "portable device" means that the patient can carry the device along so that he/she is mobile and his/her wound can nevertheless be permanently treated, i.e. without interruption. The portable device may thereby be held on the body of the patient and be carried along by means of any fastening means, for example in the form of a flexible belt or a shoulder strap. A portable device of the above-mentioned type naturally may also be used for stationary operation, i.e. detached from the body of the patient. In this case, it may e.g. be mounted to a hospital bed or be deposited next to the hospital bed.

SUMMARY OF THE INVENTION

Up-to-date negative pressure wound therapy devices are usually capable of managing different therapy situations. The devices can accommodate complex treatment procedures set by the user. This is achieved by a microprocessor based control system, which integrates inputs, such as the user settings or sensor signals, and converts it into outputs, such as suction pump control signals, vent control signals, alarm signals or display messages. The user of the device predetermines a target pressure to be applied at the wound by entering the treatment parameters into the user interface of the apparatus. The control system is programmed to generate and maintain the target pressure in its internal fluid system which is in fluid communication with the wound. The target pressure may be a constant negative pressure or a varying negative pressure. In order to avoid any discrepancies between the negative pressure predetermined by the therapy scheme and the pressure actually applied to the wound tissue, it is necessary to monitor the pressure permanently. The pressure measurements serve as an input for the control system of the device to adjust pump activity accordingly. Typically, a negative pressure device has a pressure sensor, which is present inside of the housing of the apparatus. In this case, the pressure sensor is very close to the negative pressure source (pump) and remote from the wound space. However, a pressure sensor located near the pressure source will signal a higher negative pressure (i.e. the difference between the measured pressure and the surrounding atmosphere is higher) than the negative pressure that is actually present at the wound, because there is a pressure gradient through the fluid system. In particular, a drop between the pressure source and the wound space appears.

Measuring the accurate pressure at the wound tissue can only be accomplished by a pressure sensor at or near the wound space. It is also known from the prior art to connect a pressure sensor present inside of the negative pressure unit (i.e. near the pressure source) with the wound space by a separate "pressure monitoring tube". However, locating an air pressure sensor at the wound site as well as providing an additional pressure monitoring tube increases complexity and costs of the negative pressure therapy system.

Based on a device for providing a negative pressure for medical applications, whereby the device has a pressure sensor located near the pressure source, is the underlying purpose of the present invention to further improve therapy.

In particular, it is desired to optimize accuracy and operational safety of the device. The therapy device should be able to implement a predetermined therapy scheme exactly and in a reproducible manner. Any discrepancies between the predetermined pressure and the pressure actually applied to the wound should be minimized.

A solution for the aforementioned problems is provided by the present invention. The inventors of the present invention found a novel wound pressure estimation method, which provides a suitable alternative to directly measuring the pressure at the wound site.

According to a first aspect the invention, a method of estimating a negative pressure at a wound site during a negative pressure wound therapy is proposed. Said method, which is designated in the present specification as the "wound pressure estimation method", comprises the following steps:
  i. determining a negative pressure value by means of a pressure sensor, wherein the pressure sensor is located in a fluid path between the wound site and an electrical pump, said electrical pump being used for generating a negative pressure,
  ii. determining a pump speed associated with the electrical pump,
  iii. multiplying the pump speed by a constant to obtain a modification value,
  iv. combining said modification value with the negative pressure value determined by means of the pressure sensor to obtain a modified negative pressure value corresponding to the estimated negative pressure present at the wound site.

Usually, the negative pressure value (step i.) and the pump speed (step ii.) are determined at the same time by means of, for example, the pressure sensor and the tachometer of the negative pressure wound therapy system carrying out the wound pressure estimation method.

The wound pressure estimation method works sufficiently well for practical purposes. When comparing the pressure values produced by the novel estimation method with the actual pressure at the wound site (determined under experimental conditions and by using an additional pressure sensor at the wound site) only minor discrepancies were detected.

The second aspect of the invention pertains to a negative pressure wound therapy system. The negative pressure wound therapy system according to the second aspect of the invention comprises an electrical pump for generating negative pressure, optionally a tachometer for determining a pump speed associated with the electrical pump, a pressure sensor for determining negative pressure values, a controller for controlling activity of the electrical pump, input means for adjusting settings on the negative pressure wound therapy system, said input means being operable by the user of the negative pressure wound therapy system, and a first fluid path fluidly connectable to a wound site and to the electrical pump such that the wound site can be subjected to a negative pressure. The pressure sensor is located in the first fluid path between the wound site and the electrical pump. The negative pressure wound therapy system according to the second aspect of the invention is characterized in that the controller of the negative pressure wound therapy system is adapted to execute a method according to the first aspect of the invention.

A negative pressure wound therapy system having a pressure controller which is adapted to execute the wound pressure estimation method works reliably and accurately. The system implements any predetermined negative pressure wound treatment schemes in a reproducible manner and under all typical medical treatment situations. Pressure estimation is not impaired by wound size or by extensive amounts of wound exudate. A negative pressure wound therapy system according to the second aspect of the invention can be designed robustly and simply, because additional components (such as an additional pressure sensor or an additional fluid system for pressure monitoring) are not required.

DEFINITIONS

As explained previously, the term "negative pressure" as used in connection with the present invention, defines an air pressure that is lower than the ambient air pressure (atmospheric air pressure). In the field of negative pressure therapy of wounds, the negative pressure is quantitatively defined as the pressure difference between ambient air pressure and the air pressure within the fluid path of the npwt system, in particular the air pressure applied below the cover material of the npwt dressing. For example, a negative pressure of 125 mmHg determined by means of a pressure sensor located in the fluid path of an npwt system indicates that the pressure at the pressure sensor location has been reduced by 125 mmHg compared to the ambient air pressure surrounding the npwt system. In general, negative pressure values are provided with a positive algebraic sign in this specification.

In general, a pressure gradient ($\Delta P/\Delta t$ or $dP/dt$) indicates a change in pressure which occurs in a certain period of time. For example, a negative pressure gradient of 2 mmHg/s may indicate an increase of negative pressure with a rate of 2 mmHg per second.

A target negative pressure is a negative pressure value selected by the user of the npwt system. Accordingly, the target negative pressure indicates the negative pressure value, which should be established during wound treatment. Preferably, target negative pressure values between 10 mmHg and 150 mmHg are used for negative pressure wound therapy.

Similarly, a target negative pressure gradient indicates a negative pressure gradient which should be established during wound treatment.

A negative pressure error is a pressure difference between two pressure values, for example between a measured negative pressure value and a target negative pressure value. In general, a pressure difference is calculated by performing a subtraction of the corresponding pressure values.

Similarly, a negative pressure gradient error is a difference between two pressure gradient values, for example between a measured negative pressure gradient and a target negative pressure gradient. Again, the difference is generally calculated by performing a subtraction of the corresponding pressure gradient values.

The controller of the negative pressure wound therapy system according to the second aspect of the invention is adapted to execute a method according to the first aspect of the invention. This means that the controller is not only capable of executing the method (e.g. by having the required processing power and memory), but also actually applies the method when the negative pressure wound therapy system is used for wound treatment. This requires that the controller is programmed to perform the algorithm of the method according to the first aspect of the invention.

PREFERRED EMBODIMENTS OF THE INVENTION

The value of the constant may vary between different negative pressure wound therapy systems. In particular, the performance and the size of the pump, the length of the suction tube, the diameter of the suction tube and (to a minor extent) also the material of the suction tube may influence the value of the constant. However, in a preferred embodiment of the wound pressure estimation method, the constant is a value selected from the range of 0.0025 mmHg/RPM to 0.0225 mmHg/RPM. In an even more preferred embodiment of the wound pressure estimation method, the constant is a value selected from the range of 0.00375 mmHg/RPM to 0.015 mmHg/RPM. In particular, the constant of the wound pressure estimation method may have a value of approximately 0.0075 mmHg/RPM.

According to a preferred embodiment of the wound pressure estimation method, the step of combining the modification value with the negative pressure value determined by means of the pressure sensor comprises or consists of subtracting the modification value from the negative pressure value determined by means of the pressure sensor. In this embodiment, the algebraic sign of the constant is usually positive. Otherwise, instead of a subtraction an addition would be performed and the negative pressure at the wound site would be estimated incorrectly.

The modified negative pressure value may be used by the controller of the negative pressure wound therapy system to establish the desired target negative pressure at the wound site. Therefore, the wound pressure estimation method may comprise a further step or may be combined with a further step in which the modified negative pressure value is used by a controller of the negative pressure wound therapy system to establish a target negative pressure at the wound site. In particular, the wound pressure estimation method may comprise a further step or may be combined with a further step in which the modified negative pressure value is used as an input variable for a pressure control method (e.g. the first or the second pressure control method disclosed herein). The pressure control method is executed by a controller of the negative pressure wound therapy system in order to establish a target negative pressure at the wound site.

According to a preferred embodiment of the second aspect of the invention, the controller of the negative pressure wound therapy system is adapted to execute the method according to the first aspect of the invention such that the negative pressure wound therapy system in its active state continuously or intermittently executes the method according to the first aspect of the invention. The negative pressure wound therapy system is in an active state when it is switched on, in particular when the negative pressure wound therapy system applies negative pressure to a wound site or maintains negative pressure at a wound site. Normally, the active state ends if the negative pressure wound therapy system is switched off. The active state may also end if an alarm situation such as a blockage condition, a canister full condition or a leakage condition occurs.

First Pressure Control Method

According to a preferred embodiment of the invention, the method according to the first aspect of the invention is used in combination with a first method for generating a negative pressure at a wound site during a negative pressure wound therapy. This first method is designated in the present specification as the "first pressure control method" and comprises the following steps:
  i. setting a target negative pressure on a negative pressure wound therapy system, said negative pressure wound therapy system being used for the negative pressure wound therapy,
  ii. determining a negative pressure value by means of a pressure sensor, wherein the pressure sensor is located in a fluid path between the wound site and an electrical pump, said electrical pump being used for generating a negative pressure,
  iii. calculating a difference between the determined negative pressure value and the target negative pressure setting to obtain a negative pressure error,
  iv. determining a target negative pressure gradient by means of a first function, wherein the first function maps the negative pressure error to the target negative pressure gradient,
  v. adjusting a control signal for the electrical pump in response to the value of the target negative pressure gradient, said control signal controls the speed of the electrical pump.

The first pressure control method is typically executed in a control loop.

According to a particularly preferred version of the first pressure control method, the first function essentially exhibits a curve progression as shown in FIG. 4.

According to a further preferred version of the first pressure control method, the control signal for the electrical pump is a signaling voltage or a pulse-width modulation signal.

Second Pressure Control Method

According to an even more preferred embodiment of the invention, the method according to the first aspect of the invention is used in combination with a second method for generating a negative pressure at a wound site during a negative pressure wound therapy. This second method is designated in the present specification as the "second pressure control method" and comprises the following steps:
  i. setting a target negative pressure on a negative pressure wound therapy system, said negative pressure wound therapy system being used for the negative pressure wound therapy,
  ii. determining a negative pressure value by means of a pressure sensor, wherein the pressure sensor is located in a fluid path between the wound site and an electrical pump, said electrical pump being used for generating a negative pressure,
  iii. calculating a difference between the determined negative pressure value and the target negative pressure setting to obtain a negative pressure error,
  iv. determining a target negative pressure gradient by means of a first function, wherein the first function maps the negative pressure error to the target negative pressure gradient,
  v. determining an actual negative pressure gradient,
  vi. calculating a difference between the actual negative pressure gradient and the target negative pressure gradient to obtain a negative pressure gradient error,
  vii. determining an integrator input by means of a second function, wherein the second function maps the negative pressure gradient error to the integrator input,
  viii. determining a control signal for the electrical pump comprising the use of an integrator, said integrator processes the integrator input and said control signal controls the speed of the electrical pump.

The second pressure control method is typically executed in a control loop.

According to preferred version of the second pressure control method, the actual negative pressure gradient is determined based on a first and on a second negative pressure value (resulting from a negative pressure measurement). The first negative pressure value is determined by means of the pressure sensor prior to step ii. (of the second pressure control method). The second negative pressure value is the negative pressure value of step ii. (of the second pressure control method). The second pressure control method is typically executed in a control loop. The aforementioned first negative pressure value may originate from a first cycle (determined in step ii. of this first cycle), wherein the aforementioned second negative pressure value may originate form a subsequent, second cycle (determined in step ii. of this second cycle). Generally, the aforementioned first negative pressure value may originate from an earlier cycle as the second negative pressure value.

According to a particularly preferred version of the second pressure control method, the first function essentially exhibits a curve progression as shown in FIG. 4 and/or the second function essentially exhibits a curve progression as one of the functions shown in FIG. 5 b.

According to another preferred version of the second pressure control method, the control signal for the electrical pump is a signaling voltage or a pulse-width modulation signal.

Typically, the integrator used for the second pressure control method processes the integrator input to an integrator output. The integrator output may be used as the control signal for the electrical pump. Alternatively, the control signal for the electrical pump may be derived from the integrator output by applying further processing steps. The integrator per se as well as its mode of action is known in the prior art, for example as a part of common PID controllers. In principle, the integrator continuously calculates the sum of the integrator input values of consecutive cycles of the second pressure control method. For example, when performing the second pressure control method over four consecutive cycles (the second pressure control method is typically executed by the npwt controller in a loop) integrator input values of 0.05, 0.1, 0.15 and −0.05 may result. Consequently, the integrator output in this example would be calculated as follows:

Integrator output=0.05+0.1+0.15+(−0.05)=0.25

First Blockage Detection Method

According to another advantageous embodiment of the invention, the method according to the first aspect of the invention is used in combination with a first method for detection of blockages appearing in the fluid system. Said first method, which is designated in the present specification as the "first blockage detection method", comprises the following steps:
i. generating a negative pressure at a wound site by means of an electrical pump,
ii. recording the negative pressure,
iii. venting the fluid path of the negative pressure wound therapy system by opening a relief valve, wherein during the ventilation the electrical pump is stopped,
iv. determining and recording a negative pressure drop during the ventilation step, wherein the negative pressure drop is determined for a predetermined period of time,
v. optionally closing the relief valve when the predetermined period of time has elapsed, wherein closing the relief valve finalizes the ventilation step,
vi. generating a blockage signal in a controller of the negative pressure wound therapy system if the negative pressure drop observed during the ventilation step (over the predetermined period of time) is less than a predetermined negative pressure drop.

Preferably, the negative pressure wound therapy system executes the first blockage detection method every 1 to 10 minutes, in particular every 5 minutes, during the negative pressure wound therapy. The blockage signal may be immediately communicated to the user of the npwt system, for example by means of an acoustic and/or visual alarm. Negative pressure wound therapy systems usually comprise a speaker and a display which may be used to generate such alarms. Instead of communicating the blockage signal immediately to the user, it might be advantageous to repeat the first blockage detection method (e.g. after 1 to 10 minutes, in particular after 2 minutes). Only if the repetition confirms the blocked condition, the alarm is generated.

Preferably, the negative pressure drop is determined by determining a difference between the negative pressure of step ii. of the first blockage detection method and the negative pressure present in the negative pressure wound therapy system when the predetermined period of time has elapsed. Preferably, the calculated difference is related to the negative pressure of step ii. of the first blockage detection method to obtain a percentage negative pressure drop. For example, a percentage negative pressure drop of 10% is obtained, if the negative pressure of step ii. is 100 mmHg and the negative pressure at the end of the predetermined period of time is 90 mmHg. The corresponding formula for this example can be summarized as follows:

Percentage negative pressure drop=((100 mmHg−90 mmHg)/100 mmHg)×100=10%

The general formula is:

negative pressure drop [in %]=((negative pressure of step ii.)−(negative pressure at the end of the predetermined period))/negative pressure of step ii.)×100

It is particularly preferred that the predetermined period of time is a value selected from the range of 20 seconds to 120 seconds. It is even more preferred that the predetermined period of time is a value selected from the range of 30 seconds to 60 seconds. It was found that a predetermined period of approximately 45 seconds is most preferred.

Preferably, the predetermined negative pressure drop is a relative (percentaged) value. Therefore, in a preferred version of the first blockage detection method, the blockage signal is generated in the controller if the negative pressure drop observed during the ventilation step is less than the predetermined negative pressure drop having a value selected from the range of 10% to 30% compared to the negative pressure of step ii. (of the first blockage detection method). In particular, the predetermined negative pressure drop may have a value of approximately 20% compared to the negative pressure of step ii. (of the first blockage detection method).

The first blockage detection method preferably further comprises eliminating the blocked condition after a blockage signal has been generated by the controller. The blocked condition is usually eliminated by the user of the negative pressure wound therapy system, i.e. for example a patient or a caregiver. To eliminate the blocked condition, the user has to, for example, replace the clogged suction conduit which causes the blocked condition.

Second Blockage Detection Method

According to another even more advantageous embodiment of the invention, the method according to the first aspect of the invention is used in combination with a second method for detection of blockages appearing in the fluid system. Said second method, which is designated in the present specification as the "second blockage detection method", comprises the following steps:
i. generating a negative pressure at a wound site by means of an electrical pump, ii. recording the negative pressure, iii. venting the fluid path of the negative pressure wound therapy system by opening a relief valve, wherein during the ventilation the electrical pump is stopped, iv. closing the relief valve when the negative pressure has dropped by a predetermined value, wherein closing the relief valve finalizes the ventilation step, v. determining and recording a negative pressure gradient occurring during the entire ventilation step (average negative pressure gradient during the ventilation step), vi. reactivating the electrical pump to reestablish the negative pressure of step ii., vii. determining and recording a number of pump turns, which are required to reestablish the negative pressure of step ii., viii. generating a first or a second blockage detection data set, said first or said second blockage detection data set comprising the recorded negative pressure of step ii., the recorded negative pressure gradient occurring during the entire ventilation step and the recorded number of pump turns, which were required to reestablish the negative pressure of step ii., ix. executing a classification algorithm which allows to discriminate a first blockage detection data set, said first blockage detection data set being correlated to an unblocked condition of the negative pressure wound therapy system, from a second blockage detection data set, said second blockage detection data set being correlated to a blocked condition of the negative pressure wound therapy system.

The number of pump turns in step vii. may be derived from pump speed measurements.

If the recorded negative pressure of step ii., the recorded negative pressure gradient and the recorded number of pump turns are directly used for the classification algorithm, the step of generating a first or a second blockage detection data set only consists of a compilation of these variables to form a single (first or second) data set, said (first or second) data set being used for the classification algorithm. In this case, the step of generating the first or the second blockage detection data set does not necessarily have to include any further activity of the npwt system (i.e. the controller) since the values of the three aforementioned variables have already been recorded by the system.

Preferably, the recorded negative pressure of step ii., the recorded negative pressure gradient and/or the recorded number of pump turns may be mathematically processed as will be explained more in detail below. According to these preferred embodiments, the step of generating the blockage detection data set may include further mathematical operations. Each first or second blockage detection data set which has been generated by using the recorded negative pressure of step ii., the recorded negative pressure gradient and the recorded number of pump turns, is a first or a second blockage detection data set according to the present invention (irrespective whether these variables are further mathematically processed and/or combined with each other or not).

It is recommended to express the predetermined negative pressure value as a relative (percentaged) value. According to a preferred version of the second blockage detection method, the relieve valve closes when the negative pressure has dropped by the predetermined value selected from the range of 10% to 30% compared to the negative pressure of step ii. of the second blockage detection method. In particular, the relieve valve closes when the negative pressure has dropped by the predetermined value of approximately 20% compared to the negative pressure of step ii. of the second blockage detection method. In order to close the valve immediately after the predetermined pressure drop has occurred (by for example 20%), the negative pressure wound therapy system monitors the negative pressure by permanently performing pressure measurements. These pressure measurements may also be used to determine a pressure gradient. The following example refers to the pressure gradient of step v.

Determining the negative pressure gradient may include comparing a first pressure measurement at the start of the ventilation step (typically the recorded negative pressure of step ii.) and a second pressure measurement at the end of the ventilation step. For example, the first pressure measurement may determine a negative pressure value of 100 mmHg and the second pressure measurement may determine a negative pressure value of 80 mmHg, wherein the measurements have been determined in a time interval of 10 seconds. The negative pressure gradient in this example then amounts to −2 mmHg/s. The negative algebraic sign of the negative pressure gradient can be used to indicate that the gradient is related to a negative pressure drop. The corresponding formula for this example can be formulated as follows:

Negative pressure gradient: (80 mmHg−100 mmHg)/ 10 seconds=−2 mmHg/s

According to an even more advanced version of the second blockage detection method the system monitors whether the negative pressure drop is actually accomplished within a predetermined period of time. This predetermined period of time in the second blockage detection method may have a value selected from the range of 20 seconds to 120 seconds. Preferably, the range for the predetermined period of time in the second blockage detection method is 30 seconds to 60 seconds. In particular, the predetermined period of time in the second blockage detection method is approximately 45 seconds. If the negative pressure drop is not accomplished within the predetermined period of time, this observation alone may already be sufficient to determine a blockage condition. A blockage signal may then immediately be generated in the controller of the negative pressure wound therapy system (as suggested in the first blockage detection method).

According to a preferred version of the second blockage detection method, the first or the second blockage detection data set comprises a variable $x_B$, which corresponds to (or is derived from) the recorded negative pressure of step ii. of the second blockage detection method, a variable $y_B$, which corresponds to (or is derived from) the recorded negative pressure gradient occurring during the entire ventilation step and a variable $z_B$, which corresponds to (or is derived from) the recorded number of pump turns that were required to reestablish the negative pressure of step ii. of the second blockage detection method.

According to an even more preferred version of the second blockage detection method, the variable $y_B$ is derived from the recorded negative pressure gradient by relating the recorded negative pressure gradient to a negative pressure value obtained by calculating $(0.5 \times (P_S + P_D))$. $P_S$ is or corresponds to the negative pressure of step ii. of the second blockage detection method. $P_D$ is or corresponds to the negative pressure at the end of the ventilation step. The formula to calculate the variable $y_B$ can be described as follows:

$$y_B = \text{(negative pressure gradient)} / (0.5 \times (P_S + P_D))$$

If, for example, the negative pressure gradient is at −2 mmHg/s, $P_S$ is at 100 mmHg and $P_D$ is at 80 mmHg, $y_B$ according to this preferred embodiment amounts to $-1/45$ s$^{-1}$.

$$y_B = (-2 \text{ mmHg/s}) / (0.5 \times (100 \text{ mmHg} + 80 \text{ mmHg})) = (-1/45) \text{ s}^{-1}$$

The variable $y_B$ according to this preferred embodiment may be regarded as a negative pressure gradient which is subjected to a mathematical transformation to obtain a "relative negative pressure gradient". Such a mathematical transformation may improve the use of data sets by a support vector machine (svm) algorithm. It is, for example, possible to generate a flat and uniform separation plane by said support vector machine using the mathematically transformed data. Instead, the separation plane would comprise a curved conformation if the very same data set had been used without further processing (i.e. without the mathematical transformation). The support vector machine and the separation plane may be part of the classification algorithm as mentioned below in connection with a particularly preferred version of the second blockage detection method.

To further improve application of the support vector machine, the variable $z_B$ may also be subjected to a mathematical transformation. Therefore, according to a particularly preferred version of the second blockage detection method, the variable $z_B$ is derived from the recorded number of pump turns by relating the recorded number of pump turns to the negative pressure drop during the ventilation step (or in other words by relating the recorded number of pump turns to the amount of the negative pressure increase to reestablish the negative pressure prior the ventilation step). The corresponding formula can be summarized as follows:

$$z_B = \text{(number of pump turns)} / (P_S - P_D)$$

Again, $P_S$ is or corresponds to the negative pressure of step ii. of the second blockage detection method and $P_D$ is or corresponds to the negative pressure at the end of the ventilation step. If, for example, the number of pump turns amounts to 20, $P_S$ amounts to 100 mmHg (which corresponds to the negative pressure to which the system is initially regulated after the ventilation step and up to which the number of pump turns is recorded) and $P_D$ amounts to 80 mmHg, $z_B$ according to this preferred embodiment possesses a value of 1 mmHg$^{-1}$.

$$z_B = 20 / (100 \text{ mmHg} - 80 \text{ mmHg}) = 1 \text{ mmHg}^{-1}$$

Therefore, the transformed variable $z_B$ in the aforementioned example indicates that an average of 1 pump turn per mmHg of negative pressure was required to reestablish the negative pressure of step ii. of the second blockage detection method.

According to an advantageous version of the second blockage detection method, the classification algorithm includes a support vector machine to generate a hyperplane. In other words, the classification algorithm preferably includes a hyperplane generated by a support vector machine. The basic principle of a support vector machine and a hyperplane is explained in more detail in the part of the description relating to FIGS. 8 *a* to *c*.

In particular, the classification algorithm of the second blockage detection method includes a support vector machine using a three-dimensional space and a separation plane (hyperplane). This separation plane may advantageously be a flat separation plane. In the case of the three-dimensional support vector machine, the first dimension of the three-dimensional space is preferably defined by the recorded negative pressure of step ii. of the second blockage detection method. The first dimension of the three-dimensional space may also be a variable derived from the recorded negative pressure of step ii. of the second blockage detection method. The second dimension of the three-dimensional space is preferably defined by the recorded negative pressure gradient during the ventilation step. The second dimension of the three-dimensional space may also be a variable derived from the recorded negative pressure gradient during the ventilation step. Finally, the third dimension of the three-dimensional space is preferably defined by the recorded number of pump turns or a variable derived from the recorded number of pump turns. Moreover, executing such a classification algorithm preferably comprises evaluating the blockage detection data set by determining whether the data point in the three-dimensional space associated with the blockage detection data set is on one or on the opposite side of the separation plane. The separation plane separates data points correlated to unblocked conditions from data points correlated to blocked conditions of the negative pressure wound therapy system.

According to another preferred version of the second blockage detection method, a blockage signal in a controller of the negative pressure wound therapy system is generated once the classification algorithm detects a blocked condition. Preferably, the negative pressure wound therapy system executes the second blockage detection method every 1 to 10 minutes, in particular every 5 minutes, during the negative pressure wound therapy. As in the case of the first blockage detection method, the blockage signal may be immediately communicated to the user of the npwt system, for example by means of an acoustic and/or visual alarm. Instead of communicating the blockage signal immediately to the user, it might be advantageous to repeat the second blockage detection method (e.g. after 1 to 10 minutes, in particular after 2 minutes). The alarm is generated only if the repetition confirms the blocked condition. Typically, the negative pressure wound therapy system according to the invention simultaneously executes the first and the second blockage detection method. Depending on whether the required pressure drop occurs in the pre-set time interval or not, a blockage condition is detected by the system either by the first or by the second blockage detection method.

The second blockage detection method preferably further comprises eliminating the blocked condition after a blockage signal has been generated by the controller. The blocked condition is usually eliminated by the user of the negative pressure wound therapy system, i.e. for example a patient or a caregiver. To eliminate the blocked condition, the user possibly has to replace the clogged suction conduit which causes the blocked condition.

Canister Full Detection Method

According to another very advantageous embodiment of the invention, the method according to the first aspect of the invention is used in combination with a method for detection of a canister full condition. A canister full condition appears if the exudate container of the negative pressure device is completely filled with fluids sucked from the wound space such that its intake capacity is exhausted. Said detection method is designated in the present specification as the "canister full detection method" and comprises the following steps, which are performed during a negative pressure wound therapy:

i. determining and recording a number of pump turns associated with an electrical pump used for generating a negative pressure in the negative pressure wound therapy system, wherein the number of pump turns is determined (and recorded) for a predetermined period of time, ii. determining and recording a plurality of negative pressure values by means of a pressure sensor, wherein the plurality of negative pressure values is determined (and recorded) for the predetermined period of time, iii. calculating and recording a negative pressure variation score by means of the recorded negative pressure values of method step ii., iv. generating a first or a second canister full detection data set, said first or said second canister full detection data set comprising the recorded number of pump turns and
the recorded negative pressure variation score, v. executing a classification algorithm which allows to discriminate a first canister full detection data set, said first canister full detection data set being correlated to a canister not full condition of the negative pressure wound therapy system, from a second canister full detection data set, said second canister full detection data set being correlated to canister full condition of the negative pressure wound therapy system.

The number of pump turns in step i. may be derived from pump speed measurements during the predetermined period of time. Normally, the pump speed (step i.) and the negative pressure values (step ii.) are determined for the same (predetermined) period of time, that is the measurements for step i. and for step ii. are carried out simultaneously. The plurality of negative pressure values will usually comprise a high number of negative pressure values (for example approximately 300 for 3 seconds) since electronic pressure sensors usually work with a high pressure sampling rate and this may improve the accuracy of the canister full detection method.

If the number of pump turns and the recorded negative pressure variation score are directly used for the classification algorithm, the step of generating a first or a second canister full detection data set only consists of a compilation of these variables to form a single (first or second) data set, said (first or second) data set being used for the classification algorithm. In this case, the step of generating the first or the second canister full detection data set does not necessarily have to include any further activity of the npwt system (i.e. the controller) since the values of the two aforementioned variables have already been recorded by the system.

It may however be advantageous to mathematically process the recorded number of pump turns and/or the recorded negative pressure variation score. Accordingly, the step of generating the first or the second canister full detection data set may include further mathematical operations. Each first or second canister full detection data set, which has been generated as explained above, is a canister full detection data set according to the present invention (irrespective whether the variables pump turns and pressure variation score are further mathematically processed and/or combined with each other or not).

When using the novel canister full detection method disclosed herein it has been found to be very advantageous when the predetermined period of time is a value selected from the range of 1 second to 15 seconds. It is even more advantageous when the predetermined period of time is a value selected from the range of 1 second to 6 seconds. In particular, the predetermined period of time in the canister full detection method is approximately 3 seconds.

In general, the negative pressure variation score provides an indication of the overall pressure change within the fluid-tight sealed components of the npwt system during the predetermined period of time. According to a preferred version of the canister full detection method, the calculation of the negative pressure variation score comprises the steps of i. calculating a plurality of pressure differences by means of the negative pressure values recorded during the predetermined period of time to obtain one or more negative pressure increments and one or more negative pressure decrements, wherein for calculating of each pressure difference preferably two consecutively determined negative pressure values are used, ii. calculating the sum of the negative pressure increments to obtain a single value representing the degree of the negative pressure increments, iii. calculating the sum of the negative pressure decrements to obtain a single value representing the degree of the negative pressure decrements, iv. calculating the product of the single value representing the degree of the negative pressure increments and of the single value representing the degree of the negative pressure decrements, v. optionally extracting a square root of the absolute value of the product calculated in method step iv.

The following example illustrates the calculation of the negative pressure variation score according to this preferred embodiment:

Five negative pressure values are recorded during the predetermined period of time, namely negative pressure value 1 ($p_1$) having a value of 120 mmHg,
negative pressure value 2 ($p_2$) having a value of 110 mmHg,
negative pressure value 3 ($p_3$) having a value of 115 mmHg,
negative pressure value 4 ($p_4$) having a value of 125 mmHg, and
negative pressure value 5 ($p_5$) having a value of 120 mmHg.

Four pressure differences can be calculated based on the five negative pressure values, namely pressure difference 1 ($pd_1$) having a value of −10 mmHg ($p_2-p_1$),
pressure difference 2 ($pd_2$) having a value of 5 mmHg ($p_3-p_2$),
pressure difference 3 ($pd_3$) having a value of 10 mmHg ($p_4-p_3$), and
pressure difference 4 ($pd_4$) having a value of −5 mmHg ($p_5-p_4$).

As indicated by the algebraic signs, $pd_2$ and $pd_3$ represents negative pressure increments, wherein $pd_1$ and $pd_4$ represents negative pressure decrements. Therefore, the sum of the negative pressure increments (pd+) amounts to 15 mmHg ($pd_2+pd_3$) and the sum of the negative pressure decrements (pd−) amounts to −15 mmHg ($pd_1+pd_4$). The product (pdx) of the sum of the negative pressure increments (pd+) and the sum of the negative pressure decrements (pd−) amounts to −225 mmHg$^2$ (pd+×pd−). Extracting the square root of the absolute value of the product (pdx) yields the negative pressure variation score, which in this example amounts to 15 mmHg ($\sqrt{|pdx|}$).

In a preferred version of the canister full detection method, the first or the second canister full detection data set comprises a variable $x_C$. $x_C$ corresponds to (or is derived from) the recorded number of pump turns. In addition, the first or the second canister full detection data set according to this version comprises another variable $y_C$. $y_C$ corresponds to (or is derived from) the recorded negative pressure variation score. According to a particularly preferred version of the canister full detection method, the classification algorithm includes a support vector machine to generate a hyperplane. In other words, the classification algorithm preferably includes a hyperplane generated by a support vector machine.

In particular, the classification algorithm of the canister full detection method includes a support vector machine using a two-dimensional space and a separation line (hyperplane). This separation line may advantageously be a linear separation line. In the case of the two-dimensional support vector machine, the first dimension of the two-dimensional space is preferably defined by the recorded number of pump turns or a variable derived from the recorded number of pump turns. The second dimension of the two-dimensional space is preferably defined by the recorded negative pressure variation score or a variable derived from the recorded negative pressure variation score. Furthermore, executing such a classification algorithm preferably comprises evaluating the canister full detection data set by determining whether the data point in the two-dimensional space associated with the canister full detection data set is on one or on the opposite side of the separation line. The separation line separates data points correlated to canister not full conditions from data points correlated to canister full conditions of the negative pressure wound therapy system.

Moreover, a canister full signal is preferably generated in a controller of the negative pressure wound therapy system once the classification algorithm of the canister full detection method detects a canister full condition. The canister full signal may be immediately communicated to the user of the npwt system, for example by means of an acoustic and/or visual alarm.

The canister full detection method may also comprise a step of eliminating the canister full condition once the classification algorithm detects a canister full condition. To eliminate the canister full condition, the user of the negative pressure wound therapy system simply has to replace the canister by a new, empty canister.

Leakage Detection Method

According to another preferred embodiment of the invention, the method according to the first aspect of the invention further comprises determining a leakage condition of a negative pressure wound therapy system. The method, which is designated in the present specification as the "leakage detection method", comprises the following steps:
 i. controlling an electrical pump for generating a negative pressure,
 ii. generating a leakage signal if a pump speed associated with the electrical pump exceeds a predetermined value.

The leakage signal is usually generated in a controller of the negative pressure wound therapy system. The leakage signal may be immediately communicated to the user of the npwt system, for example by means of an acoustic and/or visual alarm. Alternatively, the signal may be communicated to the user of the npwt system with a delay, for example with a delay of 1 to 10 minutes.

Preferably, the predetermined value for the pump speed is selected of the range of 1500 RPM to 10000 RPM. Even more preferably, the predetermined value for the pump speed is selected of the range of 3000 RPM to 6000 RPM. In particular, the predetermined value is approximately 3000 RPM or approximately 4900 RPM.

The predetermined value may also advantageously be selected such that the negative pressure wound therapy system is still able to essentially maintain a desired target negative pressure when the leakage signal is generated. This may be achieved by selecting a pump speed threshold (predetermined value) as suggested previously.

When using the "leakage detection method" it is further preferred to maintain the pump speed at a predetermined constant value after the leakage signal has been generated. For example, the pump may maintain a speed of 4900 RPM after a leakage signal has been generated at this threshold value. Alternatively, it is also possible to deactivate the electrical pump after the leakage signal has been generated. Both versions may prevent an increase of the pump speed after detection of the leakage condition, which may save electrical power. Moreover, both versions may prevent the electrical pump to reach a too high operating noise.

Preferably, the leakage condition is eliminated after a leakage signal has been generated. To eliminate the leakage condition, the user of the negative pressure wound therapy system possibly has to reseal the wound dressing.

Flow Rate Estimation Method

Proceeding to another preferred embodiment of the invention, the method according to the first aspect of the invention further comprises estimating a flow rate of a negative pressure wound therapy system. The method, which is designated in the present specification as the "flow rate estimation method", comprises the following steps:
 i. controlling an electrical pump for generating a negative pressure,
 ii. estimating the flow rate as a flow rate function of a pump speed and a pump current.

Any mathematical equation for estimating the flow rate is a "flow rate function" according to the invention as long as the equation comprises the variable pump speed (or a variable derived from the pump speed) and the variable pump current (or a variable derived from the pump current).

Negative Pressure Wound Therapy System

The control methods according to the present invention are described in more detail in exemplary fashion in the form of negative pressure wound therapy systems. In principle, the components and the general structure of negative pressure wound therapy systems are known in the prior art, for example from patent publications DE 10 2009 038 130 A1, DE 10 2009 038 131 A1 and DE 10 2011 075 844 A1 of the assignee. The features of the negative pressure wound therapy systems described in the following examples may also be included in a negative pressure wound therapy system according to the second aspect of the invention.

The method according to the first aspect of the invention is preferably performed by using a negative pressure wound therapy system, which comprises
 an electrical pump for generating negative pressure,
 optionally a tachometer for determining a pump speed associated with the electrical pump,
 a pressure sensor for determining negative pressure values,
 a controller for controlling the activity of the electrical pump, input means for adjusting settings on the negative pressure wound therapy system, said input means being operable by the user of the negative pressure wound therapy system, a first fluid path fluidly connectable to a wound site and to the electrical pump such that the wound site can be subjected to a negative pressure, wherein the pressure sensor is located in the first fluid path between the wound site and the electrical pump.

In particular, the electrical (actuated) pump is a membrane pump. Membrane pumps suitable for negative pressure wound therapy systems are commercially available, for example, from the company Schwarzer Precision (Essen, Germany).

Suitable pressure sensors for the npwt system are marketed amongst others by the company Freescale Semiconductor (Eindhoven, Netherlands; e.g. pressure sensor MPXV2053DP).

The controller typically regulates the negative pressure wound therapy system such that the negative pressure wound therapy system executes the control methods disclosed in the present specification. The controller may comprise a processor (CPU) and a memory to record electronic data.

Preferred input means for adjusting settings on the negative pressure wound therapy system is a touch screen.

The negative pressure wound therapy system may further have the following additional features:

Preferably, the negative pressure wound therapy system comprises a canister for collecting liquid from the wound site. The canister is located in the first fluid path between the wound site and the electrical pump. The pressure sensor is located in the first fluid path between the canister and the electrical pump. A suitable canister is disclosed, for example, in the international patent applications WO 2014/177544 A1 and WO 2014/177545 A1.

Preferably, the negative pressure wound therapy system further comprises means for preventing liquid from entering the electrical pump, for example a moisture sensitive filter or a liquid impermeable membrane. Said means for preventing liquid from entering the electrical pump is located in the first fluid path between the canister and the pressure sensor.

It is also preferred that the negative pressure wound therapy system comprises a relief valve for venting the negative pressure wound therapy system, wherein the relief valve can be controlled by the controller, a second fluid path fluidly connectable to the wound site and the relief valve, wherein the first fluid path and the second fluid path are in fluid communication at the wound site.

For practical purposes it has been found useful to include the electrical pump, the tachometer (if present), the pressure sensor, the controller, the input means, and the relief valve in a portable negative pressure device. The means for preventing liquid from entering the electrical pump should be included in the canister, said canister being removably attachable to the negative pressure device.

Preferably, the portable negative pressure device including the canister is fluidly connectable to the wound site by means of a suction conduit and a venting conduit. The suction conduit constitutes a part of the first fluid path. The venting conduit constitutes a part of the second fluid path.

If feasible, any of the aforementioned preferred methods, embodiments or advantageous features may be used in combination with each other. Any of said combinations may be used for a negative pressure wound therapy system capable of performing a method according to the first aspect of the invention. For example, a method according to the first aspect of the invention may further include the first or second pressure control method, any one of the disclosed blockage detection methods, the canister full detection method and the leakage detection method. Such a control algorithm for a negative pressure wound therapy device would be capable of controlling the pump activity in order to achieve the desired negative pressure at the wound and to detect certain alarm situations which may occur during the negative pressure wound therapy.

The different control methods disclosed herein may also establish a favorable interaction rather than being executed by the controller independently from each other. Preferred interactions of the different control methods disclosed in the present specification are listed below.

The first or second pressure control method may be used to control the speed of the electrical pump in step i. of the wound pressure estimation method.

control the speed of the electrical pump in step i. of the first blockage detection method.

control the speed of the electrical pump in step i. of the second blockage detection method.

control the speed of the electrical pump in step vi. of the second blockage detection method.

control the speed of the electrical pump in step i. of the canister full detection method.

control the speed of the electrical pump in step i. of the leakage detection method.

control the speed of the electrical pump in step i. of the flow rate estimation method.

The wound pressure estimation method may be applied to all measured negative pressure values used for the first pressure control method.

the negative pressure value in step ii. of the first pressure control method.

all measured negative pressure values used for the second pressure control method.

the negative pressure value in step ii. of the second pressure control method.

the negative pressure values used to determine the actual negative pressure gradient in step v. of the second pressure control method.

the first and the second negative pressure value (according to a preferred embodiment of the second pressure control method) used to determine the actual negative pressure gradient in step v. of the second pressure control method.

all measured negative pressure values used for the first blockage detection method.

all measured negative pressure values used for the second blockage detection method.

all measured negative pressure values used for the canister full detection method.

the plurality of negative pressure values in step ii. of the canister full detection method.

In particular, the first and second blockage detection method may interact with each other. The interactive blockage detection method may comprise the following steps:

i. generating a negative pressure at a wound site by means of an electrical pump, ii. recording the negative pressure, iii. venting the fluid path of the negative pressure wound therapy system by opening a relief valve, wherein during the ventilation the electrical pump is stopped, iv. monitoring and recording a negative pressure drop (or negative pressure gradient) during the ventilation step,
v. if the negative pressure drop observed during the ventilation step within a predetermined period of time is less than a predetermined negative pressure drop (value), generating a blockage signal in a controller of the negative pressure wound therapy system,
vi. if the negative pressure has dropped by the predetermined value within the predetermined period of time, closing the relief valve when the negative pressure has dropped by the predetermined value to finalize the ventilation step, followed by the steps of
vii. determining and recording a negative pressure gradient occurring during the entire ventilation step (average negative pressure gradient during the ventilation step),
viii. reactivating the electrical pump to reestablish the negative pressure of step ii.,
ix. determining and recording a number of pump turns, which are required to reestablish the negative pressure of step ii.,
x. generating a first or a second blockage detection data set, said first or said second blockage detection data set comprising
the recorded negative pressure of step ii.,
the recorded negative pressure gradient occurring during the entire ventilation step and
the recorded number of pump turns, which were required to reestablish the negative pressure of step ii.,
xi. executing a classification algorithm which allows to discriminate
a first blockage detection data set, said first blockage detection data set being correlated to an unblocked condition of the negative pressure wound therapy system, from
a second blockage detection data set, said second blockage detection data set being correlated to a blocked condition of the negative pressure wound therapy system,
xii. optionally generating a blockage signal in the controller of the negative pressure wound therapy system, if a blocked condition of the negative pressure wound therapy system is detected by means of the classification algorithm.

The additional features of preferred embodiments of the first and the second blockage detection method may also be implemented in the interactive blockage detection method.

FIGURES

Further characteristics, details, and advantages of the invention result from the appended patent claims and from the drawings and the following description of preferred embodiments of the invention. The drawings show:

FIG. 1 A schematic drawing of a simple negative pressure wound therapy device including the negative pressure bandage applied to a wound of a patient.

FIGS. 2 *a* to *e* Different views of a typical portable negative pressure wound therapy device to generate a negative pressure for medical applications.

FIG. 3 A schematic drawing of the piping system and of the electronic components of a typical negative pressure wound therapy device.

FIGS. 4 *a* and *b* The first function according to a preferred embodiment of the invention.

FIGS. 5 *a* and *b* The second function according to a preferred embodiment of the invention.

FIG. 6 The second pressure control method in a schematic overview according to a preferred embodiment of the invention.

FIG. 7 The negative pressure in a npwt system during the blockage detection method according to a preferred embodiment of the invention.

FIGS. 8 *a* to *c* The blockage detection function as a part of a preferred embodiment of the invention.

FIG. 9 The canister full detection function as a part of a preferred embodiment of the invention.

FIG. 10 Experimental results concerning the leakage detection method according to a preferred embodiment of the invention.

FIGS. 11 *a* to *c* Experimental results concerning the flow rate estimation method according to a preferred embodiment of the invention.

DESCRIPTION OF THE FIGURES

A simple negative pressure wound therapy device 1, which is in fluid communication with a wound 2 of a patient to be treated is shown in FIG. 1 schematically. Wound therapy devices of this type are known in the prior art. In many cases, like the one shown in this non-limiting example, the portable negative pressure wound therapy device 1 has a container 3 adapted for receiving body fluids, in particular wound exudates extracted from the wound by suction. The container (or canister) 3 is typically made of a solid material, such as a plastic material. It is usually a disposable article designed for single use. Conveniently, the container 3 can be detachably mounted to the housing part 4 of the device, which contains the electrical and/or electronic components of the apparatus. The container 3 can be evacuated by the electrically actuated suction pump 5. A connection (not shown) is provided for a suction line 6 that leads to the wound such that negative pressure communication can be established between the suction pump 5, the container 3, and the suction line 6 that leads to the wound. A filter or air/liquid-separator 7 located within the fluid-pathway between the container 3 and the suction pump 5 is used to prevent exudate from being sucked into the pump 5. A negative pressure wound therapy device typically comprises additional components such as a control system for controlling activity of the pump and means for interacting with the user, such as a touch-screen display or control buttons. These components are not shown in FIG. 1.

In some embodiments, the portable negative pressure wound therapy device does not have a container for receiving the drained body fluids. Instead, the body fluids can be contained, for example, in the dressing. This is achieved by providing absorbent layers (not shown in FIG. 1). Such negative pressure wound therapy devices, which do not make use of a separate solid exudate canister are typically used for treating less exudating wounds, for example surgical wounds.

Figure 2C:
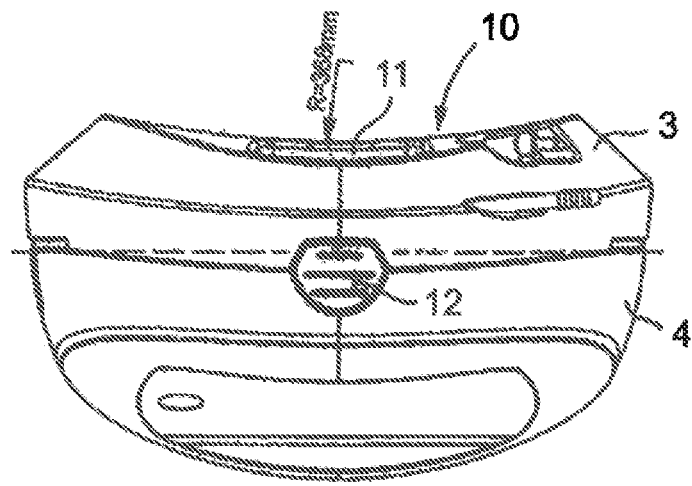
FIGS. 2 *a* to *e* show a typical example of a portable device 1 for the provision of the negative pressure for medical applications. The device 1 comprises a first housing part 4 in which a negative pressure-producing device in the form of an air suction pump 5 and electrical and electronic control components for the device are accommodated completely, including batteries or preferably rechargeable batteries. A recharging connection for the batteries is designated by reference symbol 8. Moreover, the device 1 comprises a second housing part that is also a container 3 for receiving body fluids, in particular, for receiving wound exudates suctioned away from a wound. The entire second housing part is preferably constituted as a disposable single-use item. In its upper region, a connection gland 9 for a suction tube is provided that may, for example, lead to a wound dressing that sealingly closes the wound when the device 1 is used in the negative pressure therapy of wounds and there it can, for example, communicate with the wound space through a port to apply and maintain a negative pressure to the wound space and to suction away wound exudates into the container. For this purpose, the container 3 communicates with the suction pump 5.
Figure 2D:
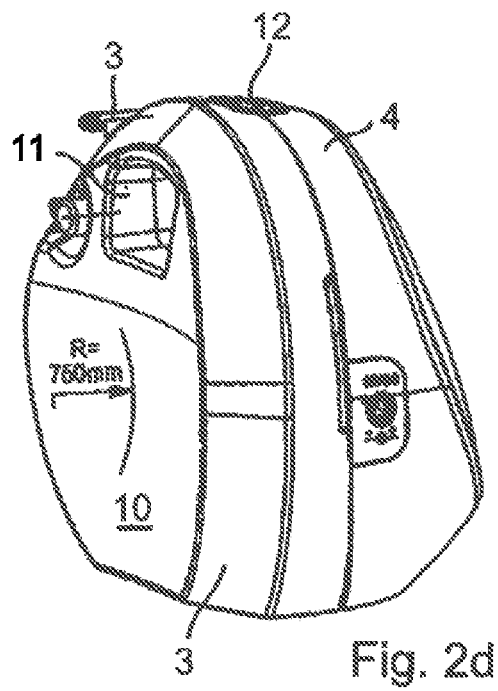
Figure 2E:
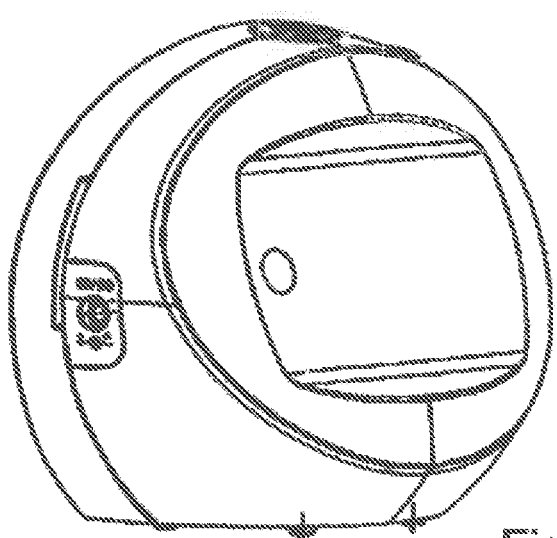

It can also be seen from FIG. 2 *d* on the side 10 of the second housing part 3 facing the body, a grip recess 11 is formed in the shape of an opening extending right through the second housing part 3. In this way, the device 1, or only its second housing part 3, can be gripped and handled with one hand.

In the preferred embodiment shown, a manually operable element 12 is provided in this grip recess 11 on the upper side of the device 1, for example, in the form of a pushbutton that acts on locking and back-gripping means (not shown). In the joined condition of the two housing parts 3 and 4, the locking or back-gripping means are in a locked condition holding the two housing parts 3, 4 together by positive action. Only on operation of the operating element 12, the lock is released so that the housing parts 3, 4 can be separated from each other.

Figure 3:
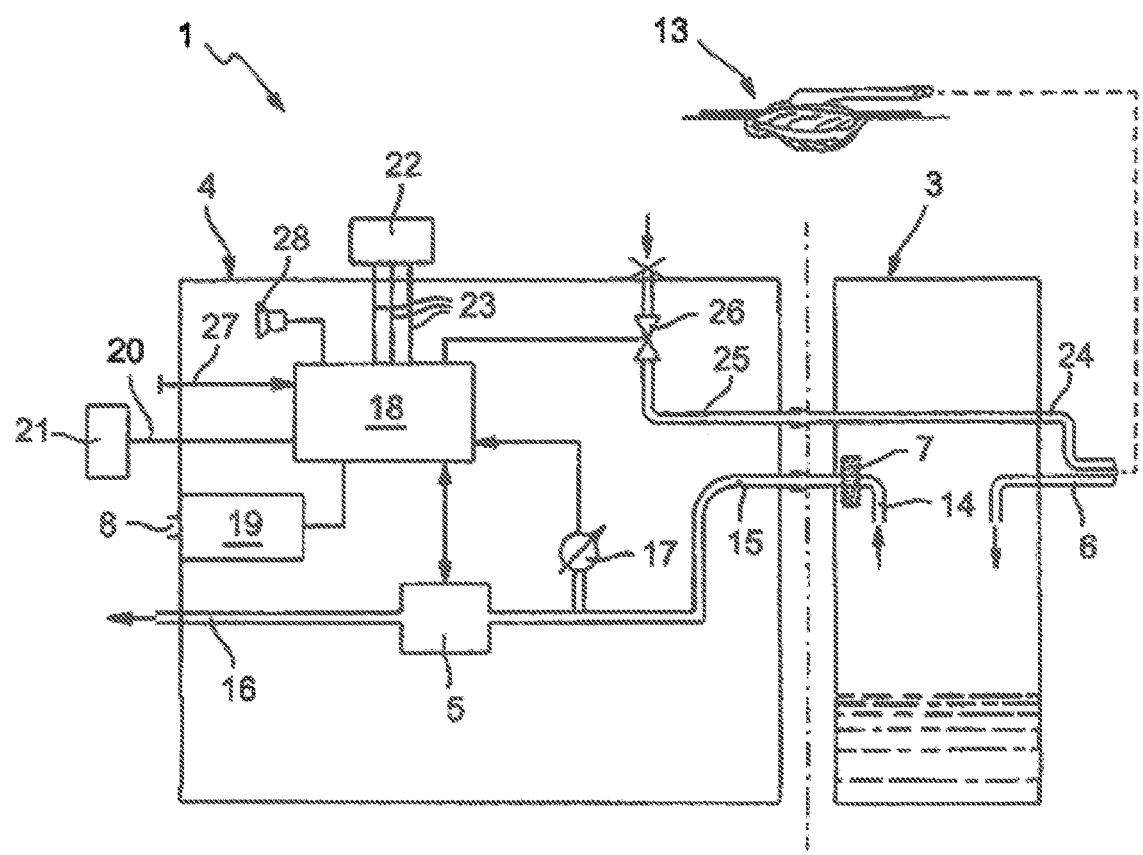

FIG. 3 shows the nature of the piping system and of the electronic components of an exemplary negative pressure wound therapy device, for which the inventive control method can advantageously be used. The device is similar to the negative pressure wound therapy device of the type exemplified in FIG. 2. In contrast to the very basic system shown in FIG. 1, the device of FIG. 3 includes additional components (known from the art) such as the air rinsing pathway of the fluid system. FIG. 3 shows the previously described device for providing a negative pressure for medical applications in a purely schematic representation, wherein relevant reference symbols are used for the corresponding components. However, FIG. 3 only shows those components that are relevant for describing the present invention. FIG. 3 shows a wound to be treated (schematically) with a negative pressure with a vacuum-tight wound dressing 13, to which the suction tube 6 emanating from the container 3 leads. From the container 3, a further tube section 14 leads outwardly through the filter 7 mentioned previously. If the container 3 or the first housing part 4 is put into its operating position on the first or basic housing part 4 of the device 1, the tube section 14 is connected to a further tube section 15 within the first housing part 4 that leads to the intake side of the suction pump 5. When the suction pump 5 operates, a negative pressure is applied to the container 3 and to the suction tube 6 via tube sections 14, 15, and air suctioned in from there is blown out to the environment via outlet tube 16, wherein additionally non-depicted sound damping elements and, if necessary, further filters can be provided.

Moreover, a pressure sensor 17 for measuring the pressure is provided in the tube section 15 between container 3 and suction pump 5. Its signals are sent to an electronic control unit 18, which performs open-loop and closed-loop control of the device 1 in total. The electronic control unit 18 comprises a microelectronic controller and at least one electronic memory. Also shown is the charging connection 8 for rechargeable batteries that are located in a compartment 19 and a connection 20 for a schematically indicated power supply unit 21. Reference symbol 22 indicates a display unit, preferably having a capacitive switch membrane (touchscreen). A user may control operation of the device via said touchscreen. The electrical connection to the electronic control unit 18 is only shown via electrical lines 23. The suction pump 5 is controlled by the electronic control unit 18 by means of the signals of the pressure sensor 17, so that the pressure value corresponding to the currently selected program is controlled in the tube section 15.

Also shown is an additional rinsing or aeration tube 24 that (according to an exemplary design) proceeds through the container 3 and just like the suction tube 6 leads to the wound dressing 13. When the container 3 is attached in its intended assembly position on the first housing part 4, this rinsing tube 24 communicates with a tube section 25 provided in the first housing part 4. The first housing part 4 comprises an electromagnetically operated valve 26 that can be actuated by the electronic control unit 18. Said valve 26 connects the tube section 25 with the atmospheric air when it is open, so that an air current toward the wound via the rinsing tube 24 can be generated.

The device 1 and its electronic control unit 18 also feature a data interface 27 (preferably a USB interface). The electronic control unit 18 can be programmed using said data interface 27. In addition, device 1 comprises a speaker 28 which is connected to the control unit 18. The speaker can be used to generate acoustic alarm signals. A user may set a target negative pressure via user interface 22. After starting the therapy a negative pressure value is determined by means of the pressure sensor 17. Pressure sensor 17 is located in a fluid path between the wound site 2 and the electrical pump 5. The electrical suction pump 5 is used for generating the negative pressure. The methods of generating a negative pressure according to aspects or preferred embodiments of the invention include calculating a difference between the negative pressure value determined by the sensor 17 and the target negative pressure setting to obtain a negative pressure error. As a consecutive step a target negative pressure gradient is derived by means of a first function. The first function maps the negative pressure error to the target negative pressure gradient. Finally a control signal is adjusted in response to the value of the target negative pressure gradient. The control signal thus obtained is used for controlling the speed of the electrical pump 5.

In the following, the novel methods for controlling a negative pressure wound therapy system are explained in more detail (FIG. 4 to FIG. 11). These control methods represent particularly important aspects of the present invention or preferred embodiments thereof. The control methods disclosed in the present specification are particularly suited for a negative pressure wound therapy system with a general structure as shown in FIG. 2 and FIG. 3. However, the control methods disclosed in the present specification may also be suited for other negative pressure wound therapy systems.

Method of Generating a Negative Pressure at a Wound Site (First and Second Pressure Control Method) Basically, the negative pressure wound therapy system is permanently determining the actual pressure present at the pressure sensor. The collected pressure values may preferably be modified by means of the "wound pressure estimation method" as explained below. The controller of the negative pressure wound therapy system then compares the determined pressure value with the "target pressure" selected by the user. The difference between the determined pressure value and the target pressure is the "pressure error". The core of the pressure control is the desired "target pressure gradient". The target pressure gradient is derived from a function. The input of said function is the pressure error. This function is herein also designated as "first function". An example for a first function is shown in FIGS. 4 *a* and *b*.

Figure 4A:
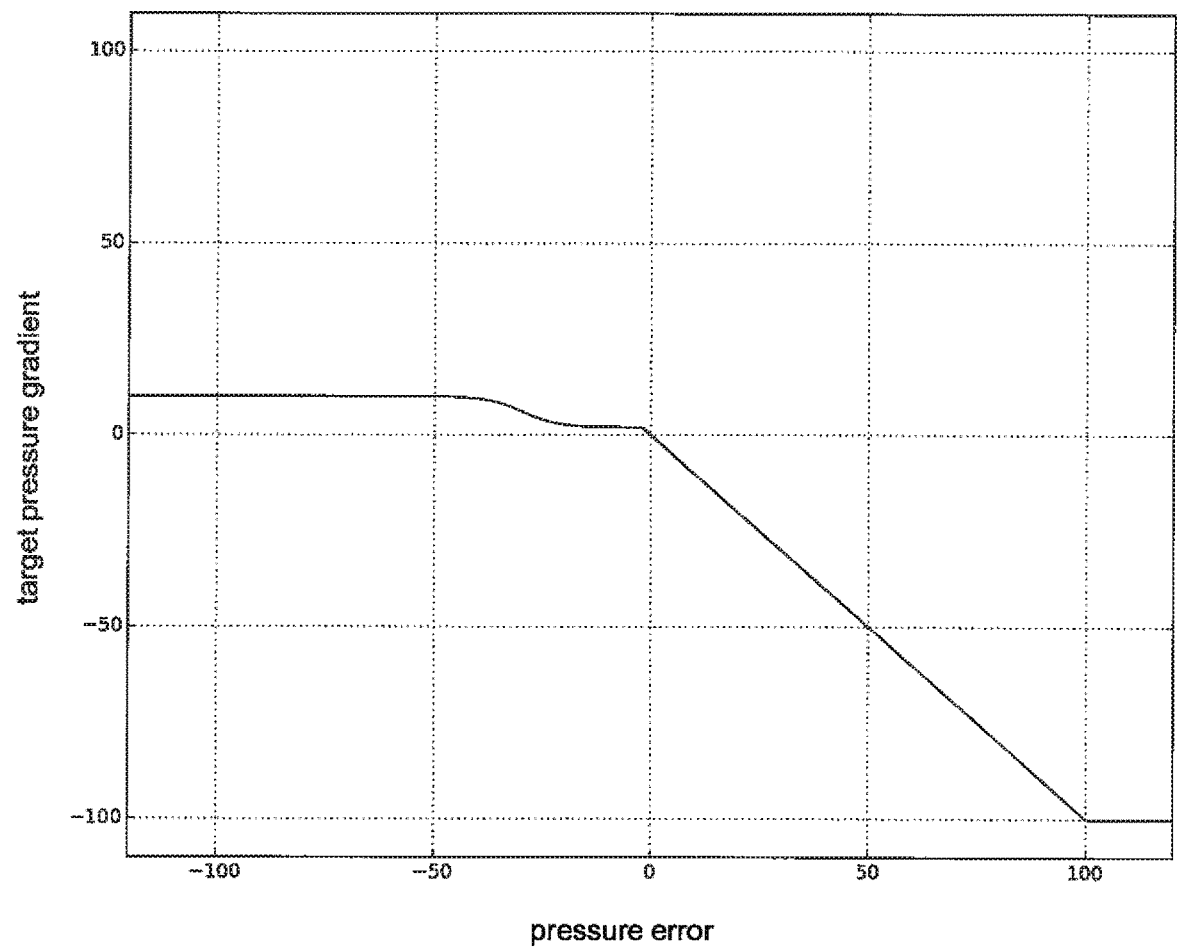
Figure 4B:
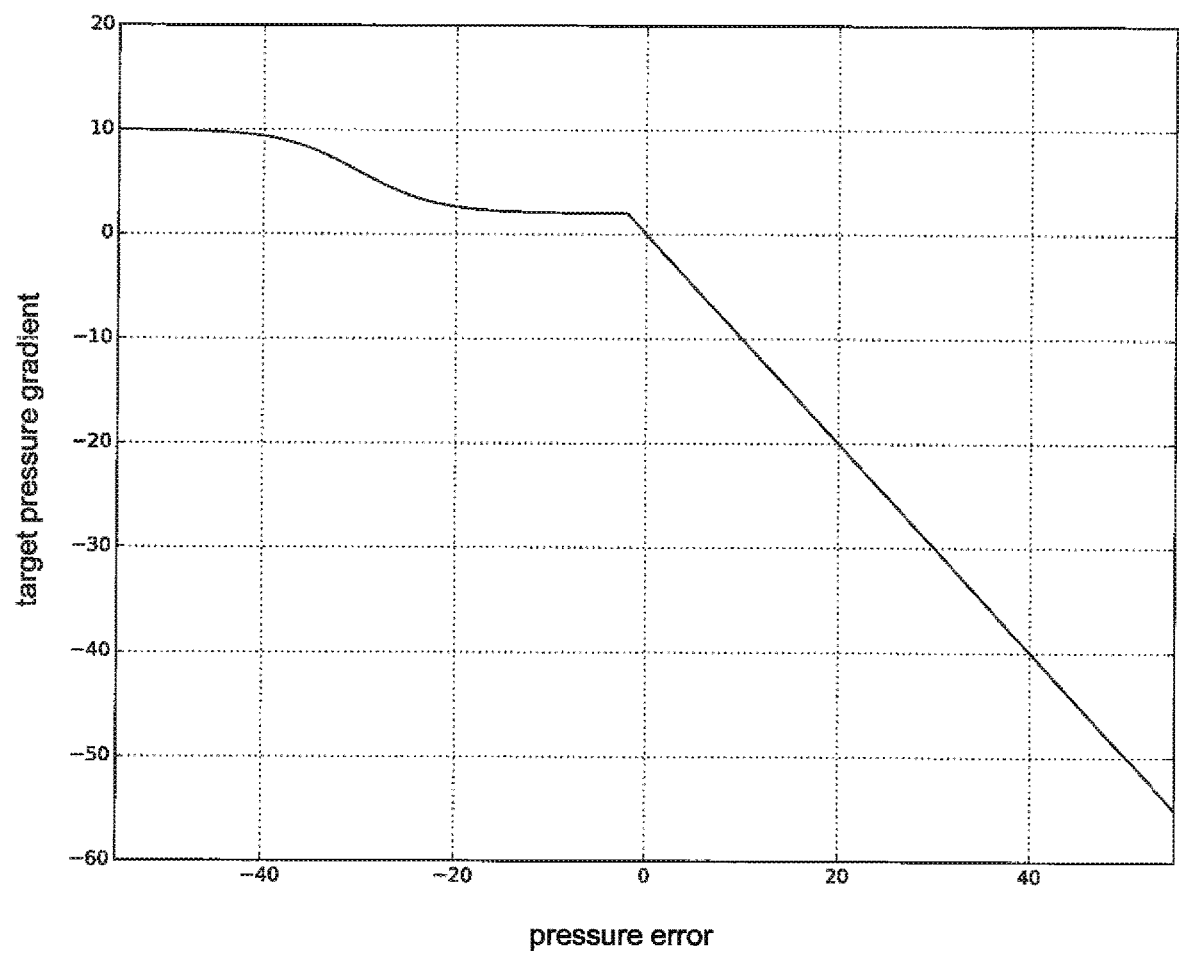

The x-axis of the diagrams included in FIGS. 4 *a* and *b* represents the pressure error (difference between the measured pressure and the target pressure). The y-axis of the diagrams in FIGS. 4 *a* and *b* represents the target pressure gradient. FIG. 4 *b* is an enlarged view of the central part of FIG. 4 *a*. As can be seen in FIGS. 4 *a* and *b*, the first function provides a linear target response with respect to pressure error values between approximately −2 mmHg and 100 mmHg. Beyond this range, the response remains either constant (pressure error >100 mmHg) or further increases (pressure error <approximately −2 mmHg) with a "S"-shaped curve progression to a maximum target pressure gradient of 10 mmHg/s. The first function (as well as the second function explained below) cannot be conveniently described by means of a single mathematical equation. The first (and the second) function may at most be described by a combination of several mathematical equations (functions).

A pressure error with a negative algebraic sign may be obtained if, for example, the measured negative pressure amounts to 115 mmHg and the target negative pressure amounts to 125 mmHg (the pressure error then amounts to −10 mmHg). In this case the npwt system has not yet achieved the target negative pressure. A pressure error with a positive algebraic sign may be obtained if, for example, the measured negative pressure amounts to 135 mmHg and the target negative pressure amounts to 125 mmHg (the pressure error then amounts to 10 mmHg). In this case too much negative pressure is present within the npwt system. In general, a target negative pressure gradient above 0 (>0) may cause an increased pump activity. Instead, a target negative pressure gradient below 0 (<0) generally may cause a decreased pump activity. The target negative pressure gradient for pressure error values exceeding −100 (for example −110) in the shown example will always amount to 10 mmHg/s. Similarly, the target negative pressure gradient for pressure error values exceeding 100 (for example 110) in the shown example will always amount to −100 mmHg/s.

The target pressure gradient taken from the first function is then compared with the actual pressure gradient yielding the "pressure gradient error". The actual pressure gradient is based on the pressure data received by the pressure sensor (which are preferably modified by the "wound pressure estimation method" as already mentioned). The pressure gradient error is the input for another function, which allows for calculating the so called "integrator input". This function, designated herein also as "second function" and exemplarily depicted in FIGS. 5 *a* and *b*, is mainly an adaptation and limitation of the signal, which finally controls the pump activity. The second function therefore provides a weighting to the integrator input based on the pressure gradient error.

Figure 5A:
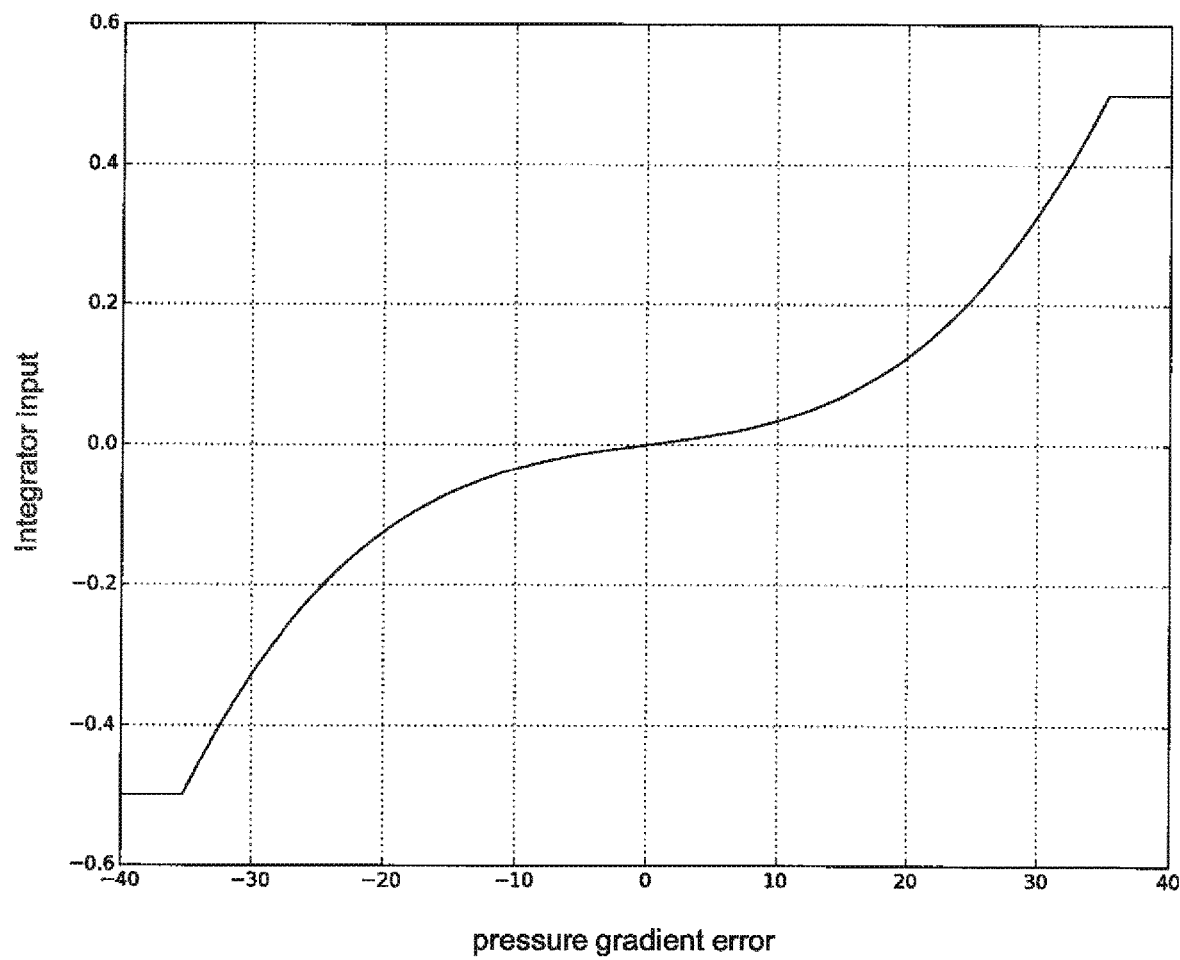
Figure 5B:
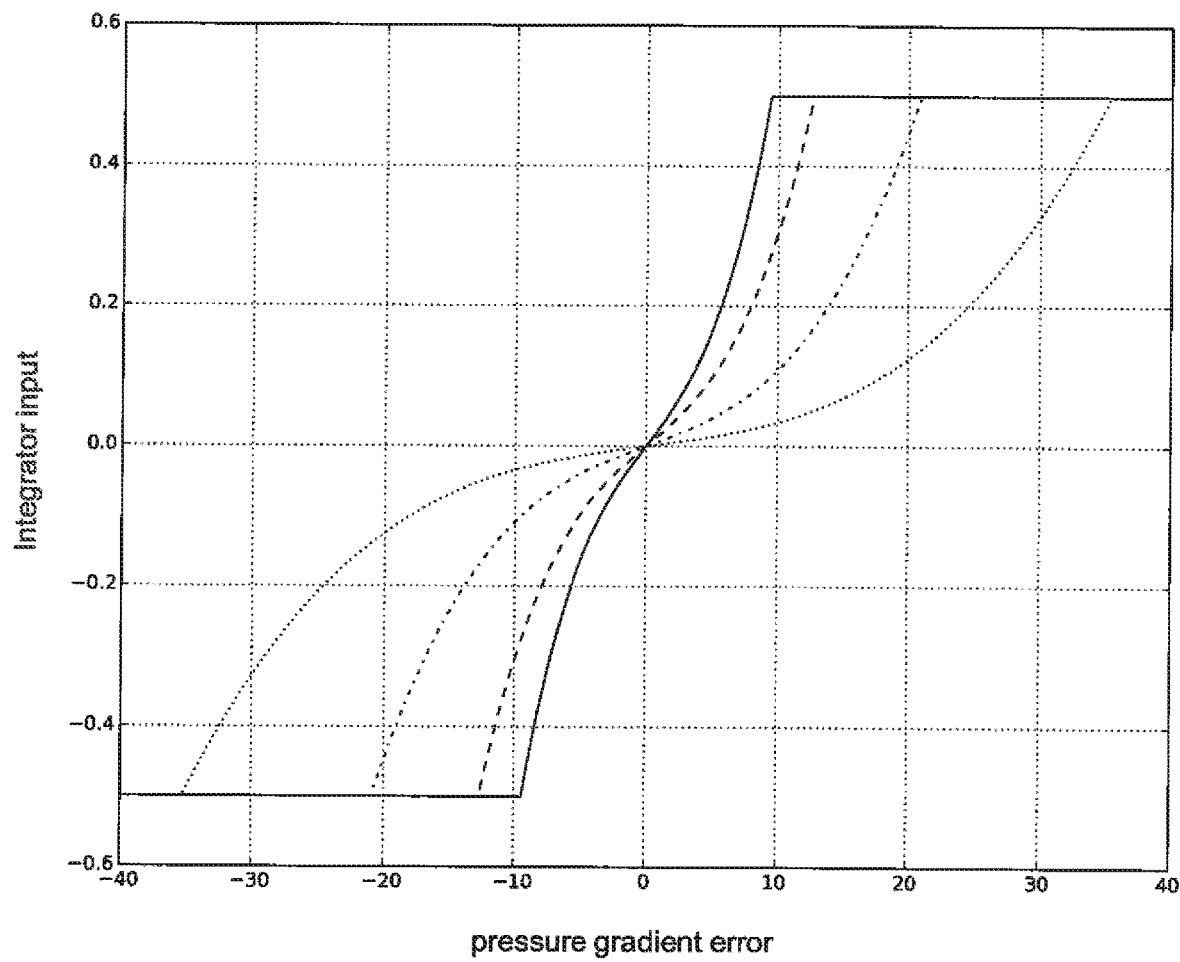

The x-axis of the diagrams in FIGS. 5 *a* and *b* relates to the pressure gradient error (difference between the measured pressure gradient and the target pressure gradient). The y-axis of the diagrams in FIGS. 5 *a* and *b* represents the integrator input. The second function shown in FIG. 5 *a* exhibits a flat "S"-shaped curve progression in the pressure gradient error range of approximately −35 mmHg to 35 mmHg. FIG. 5 *b* shows the previous second function together with three alternative versions of the second function having narrower "S"-shaped sections. The pressure control method may include only one of the shown second functions. However, adapting the second function in the course of the negative pressure wound therapy may reduce oscillations in the generated pressure and, therefore, further improve the pressure control method. For example, the controller of the npwt system may adapt the second function during the cycles of the pressure control method based on the magnitude of the pressure gradient fluctuations. Thus, depending on the magnitude of the pressure gradient fluctuations, the controller determines a particular suited second function adapted to the current circumstances which may look like one of the functions in FIG. 5 *b* (or at least look similar to the functions in FIG. 5 *b*).

A pressure gradient error with a positive algebraic sign may be obtained if, for example, the measured negative pressure gradient amounts to 1 mmHg/s and the target negative pressure gradient amounts to 2 mmHg/s (the pressure gradient error then amounts to 1 mmHg/s). In this case the npwt system has not yet achieved the target negative pressure gradient. A pressure gradient error with a negative algebraic sign may be obtained if, for example, the measured negative pressure gradient amounts to 3 mmHg/s and the target negative pressure gradient amounts to 2 mmHg/s (the pressure gradient error then amounts to −1 mmHg). In this case the negative pressure in the npwt system increases too fast. In general, an integrator input value above 0 (>0) may cause an increased pump activity. Instead, an integrator input value below 0 (<0) generally may cause a decreased pump activity. The integrator input for pressure gradient error values exceeding −40 (for example −50) in the shown examples will always amount to −0.5. Similarly, the integrator input for pressure gradient error values exceeding 40 (for example 50) in the shown examples will always amount to 0.5.

The integrator output may already constitute the control signal for the pump. Alternatively, the integrator output may be transformed (or "translated") into the final control signal for the pump. Said final control signal for the pump may be for example, the pump voltage (signalling voltage of the pump). There may exist a third or even further functions (not shown on the figures), which transforms the integrator output to the final control signal (e.g. the pump voltage) and/or further adapts the integrator output/control signal in accordance with certain pump characteristics. However, such a third or further function is not necessarily required.

The suggested pressure control algorithm effectively works as a PID controller using the target pressure gradient instead of the pressure as its primarily input.

The first function is the most important one, because it has a predominant influence on the general control performance of the pressure controller. The second function and the third function add performance improvements. By using the pressure control method suggested in the present specification, the npwt system may be able to generate and maintain the desired target negative pressures effectively but at the same time smoothly. Smooth pressure adaptations during therapy improve patient comfort.

Figure 6:
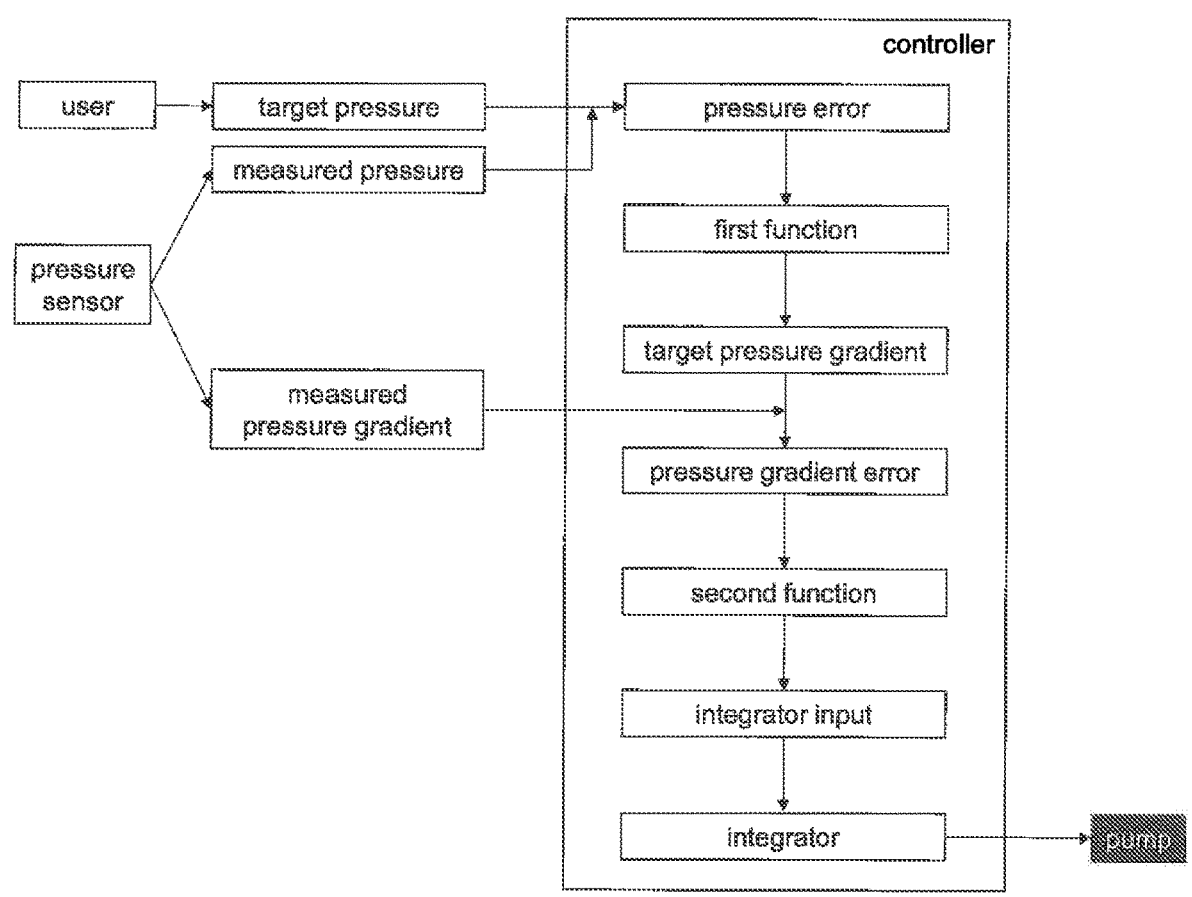

An outline of the pressure control method for generating a negative pressure at a wound site is given in FIG. 6.

Method of Estimating a Negative Pressure at a Wound Site (Wound Pressure Estimation Method)

The objective of the wound pressure estimation method is to compute a modification value which may be used to compensate for a pressure drop appearing between a pressure sensor located near a negative pressure source (pump) and a wound site. During experiments performed using a wound simulator it was unexpectedly found that the pressure drop is proportional, at least to a great extent, to the pump speed. It was also found that said pressure drop is (at least to a great extent) independent of the pressure present at the pump. It is therefore possible to get a highly reliable estimation of the pressure drop by multiplying pump speed by a constant value:

"Modification Value Formula"

modification value (mmHg) [i.e. pressure drop]=constant (mmHg/RPM)×pump speed (RPM)

The constant has to be determined empirically for each type of npwt system.

The estimated pressure drop (modification value) may then be used to estimate the pressure present at the wound:

"Pressure Estimation Formula"

estimated negative pressure at the wound (mmHg)
=measured negative pressure (mmHg)−(constant (mmHg/RPM)×pump speed (RPM))

The abbreviation RPM stands for "revolutions per minute" and is the unit of the pump speed. Typically, the pump speed is measured from the output of the pump tachometer.

In summary, the wound pressure estimation method is based on a modification value applied to the pressure data received from the pressure sensor. The pressure modification compensates for the estimated pressure drop between a pressure sensor located near a pressure source and the wound. Advantageously, the wound pressure estimation method is working continuously while the negative pressure wound therapy system is active, except during flushing (venting).

Figure 1:
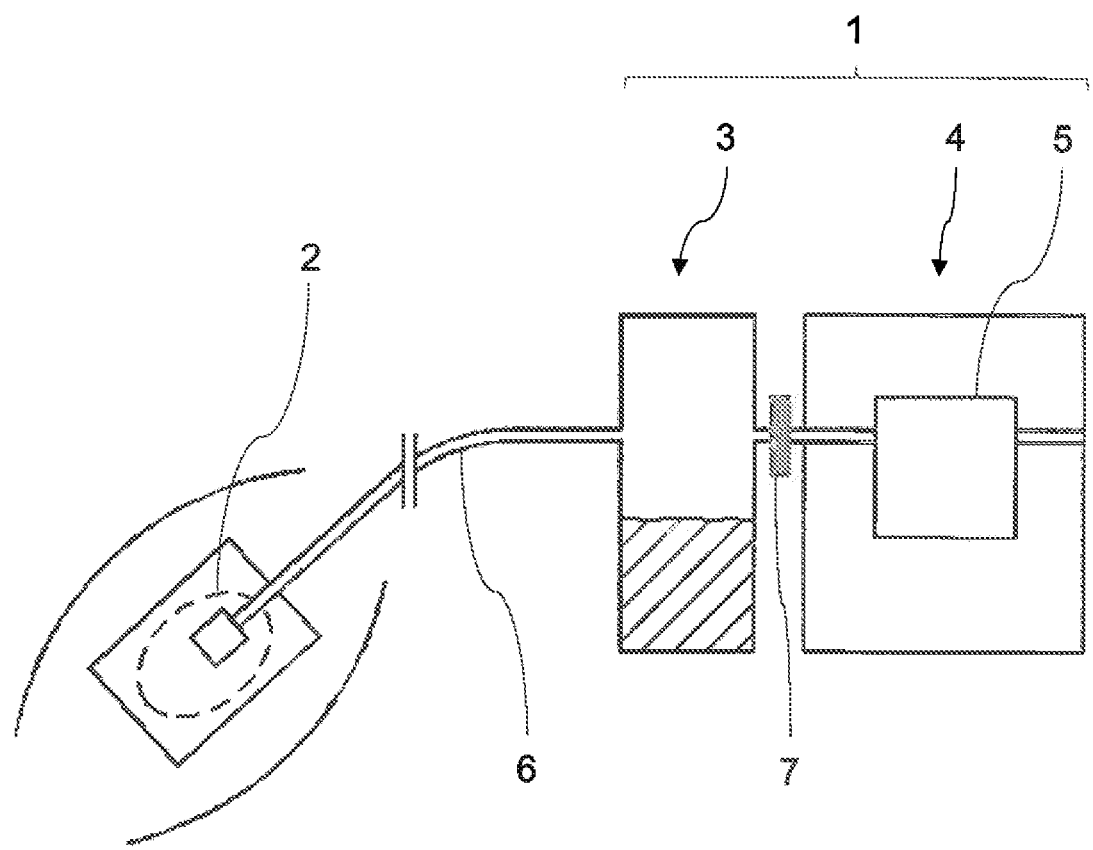

The following example illustrates application of the wound pressure estimation method by referring to the npwt systems shown in FIG. 1 and FIG. 3:

A negative pressure value of 125 mmHg is determined using pressure sensor 17. The pressure sensor is located in the fluid path between pump 5 and filter 7. The pump speed of the electrical pump 5 at the time of the pressure measurement is 1000 RPM. The constant determined for the npwt system used for the experiments is 0.0075 mmHg/RPM. Using the "pressure estimation formula" disclosed herein, the estimated negative pressure at the wound site 2 is 117.5 mmHg:

estimated negative pressure at the wound (mmHg)
=125 mmHg−(0.0075 mmHg/RPM×1000 RPM)
=117.5 mmHg The example demonstrates that the negative pressure measured near the negative pressure source is usually higher than the negative pressure actually applied to the wound site. Treating the wound at an incorrect negative pressure level may impair the efficacy of the negative pressure wound therapy.

Method of Determining a Blockage Condition in a Negative Pressure Wound Therapy System (First and Second Blockage Detection Method)

The blockage detection method of the negative pressure wound therapy system necessarily incorporates a flush (venting) procedure. Thus, the blockage detection method may advantageously be used for an npwt system having a separate fluid path for performing a venting procedure (such as the npwt system described in FIG. 3). The blockage detection method acts independently of the canister full detection method. The blockage detection method suggested in the present specification is versatile and works precisely and reliably. Moreover, the disclosed method is easy to perform once the classification algorithm has been established.

The blockage detection method according to a particularly preferred embodiment comprises the following steps:

"Pressure generation/stabilise": Regulate the negative pressure wound therapy system to a negative pressure, for example to the target negative pressure. Advantageously, the negative pressure to which the system is regulated is a "stable negative pressure". A stable negative pressure is present if, for example, the following two conditions i) and ii) are met:

i) The negative pressure exceeds a certain value, for example a value of 18.6 mmHg.

ii) The pressure gradient remains within a certain (narrow) range, for example within the range of −1 mmHg/s and 1 mmHg/s or within the range of −0.5 mmHg/s and 0.5 mmHg/s. A stable negative pressure may also be defined by different requirements. Regulating the pressure to a stable negative pressure is the object of a preferred embodiment, where it may further improve reliability of the blockage detection. Nevertheless, the stable negative pressure is not necessarily required to perform the blockage detection method.

"Evacuate/venting": Record the start pressure, open the relief valve and stop the pump. Record the pressure gradient until the pressure drops by 20% or until a 45 second timeout elapses.

"Recover & Hold": Close the relief valve and restart the pump in order to return to the pressure, which has been recorded at the start of the evacuation step. Record the number of pump turns.

"Evaluate blockage score": Evaluate a blockage score using (1) the recorded pressure at the start of the evacuate step, (2) the average pressure gradient during the evacuate step, and (3) the number of pump turns during the recover & hold step (the three variables form a blockage detection data set).

If the 45 second timeout elapses before the pressure drops by 20% during the evacuate step, the blockage detection method is terminated and a tube blockage signal is set (the alarm signal, however, is preferably only released after the tube blockage is finally verified, see below).

Figure 8A:
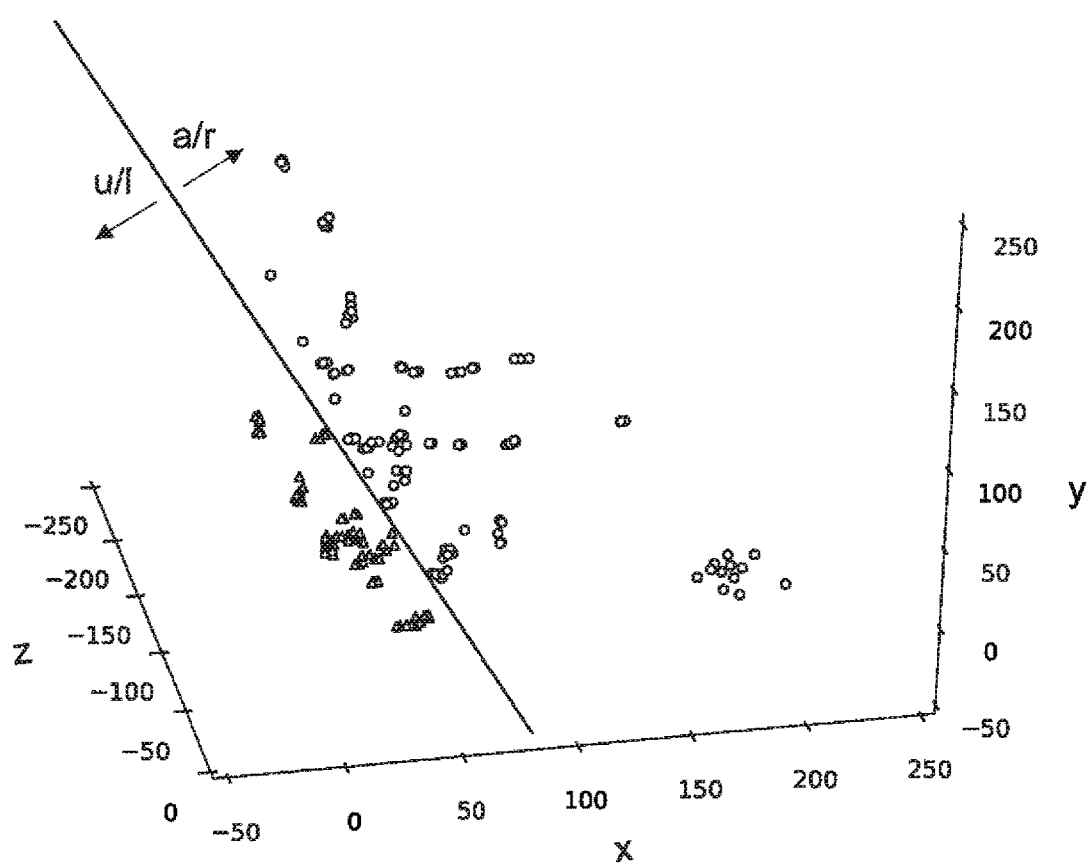
Figure 8B:
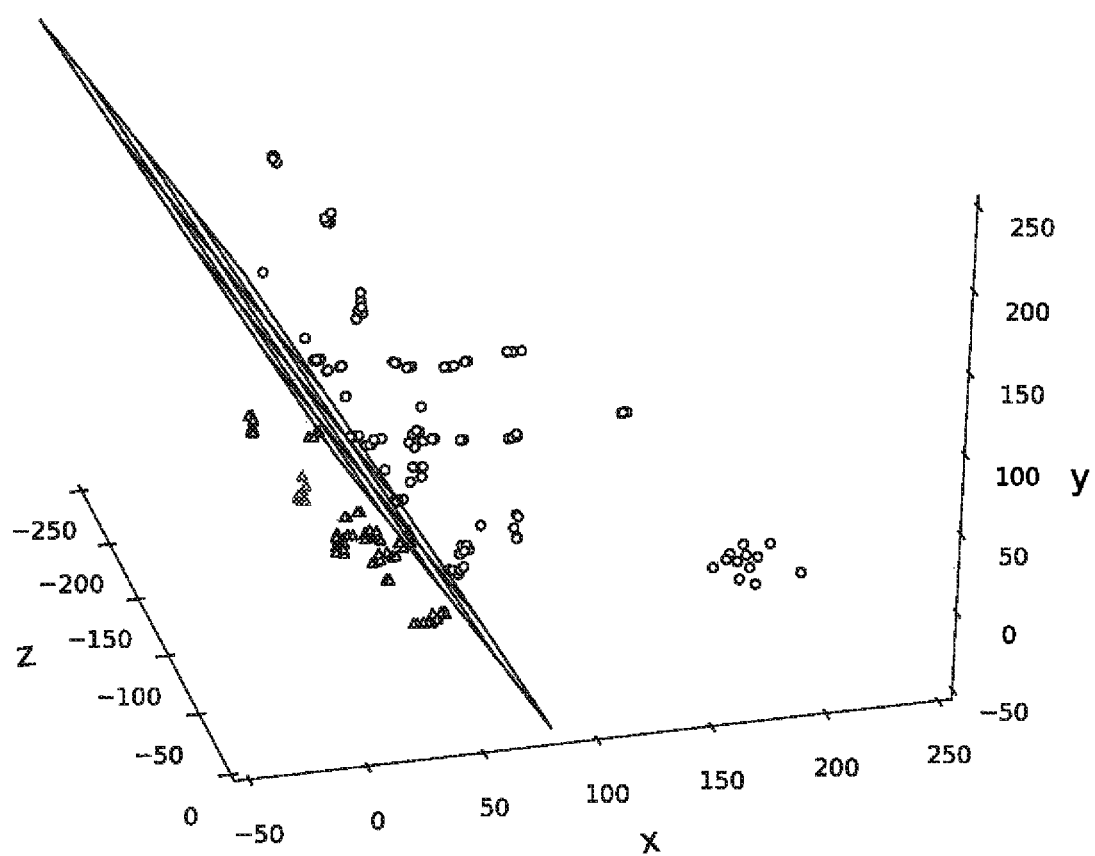
Figure 8C:
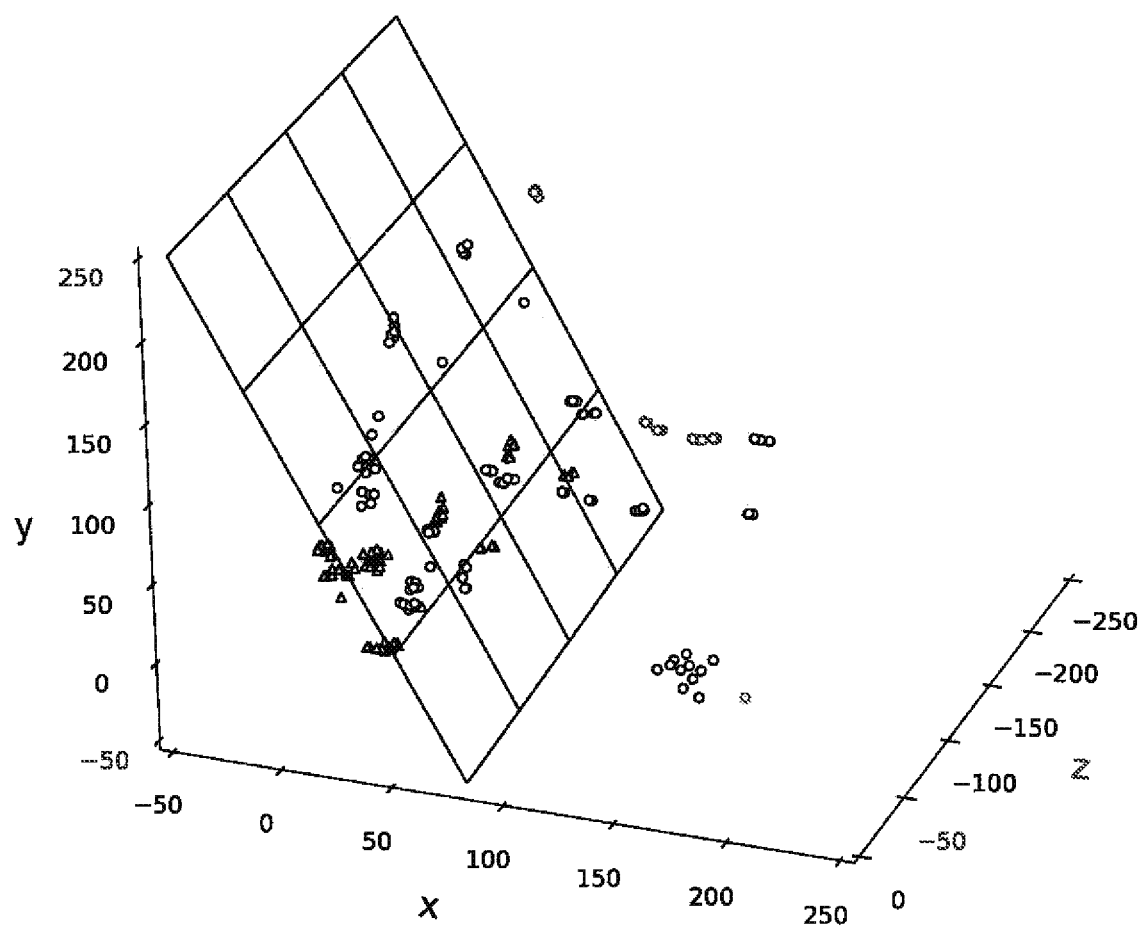

If the pressure drops by 20% within 45 seconds during the evacuation step (leading to a regular termination of the flush procedure), the blockage detection data set is evaluated. Said evaluation is done using a linear function which describes a plane in 3D space that separates "blocked" points (second blockage detection data sets) from "unblocked" points (first blockage detection data sets) derived from the aforementioned variables (1), (2) and (3). An exemplary blockage detection function is depicted in FIGS. 8 a to c. If the evaluation results in a detection of a blockage condition, a tube blockage signal is set.

The tube blockage detection method may be active, for example, every five minutes. When a tube blockage signal is set, the tube blockage detection method is preferably repeated after two minutes to re-evaluate the blockage condition. If the tube blockage is verified, an alarm is displayed to the user. In this example, a user receives the alarm not later than 7 minutes after the blockage initially appeared. The alarm informs the user that a blockage condition exists in the negative pressure wound therapy system. The user may then initiate the necessary steps to eliminate the blockage condition, for example by replacing the suction conduit being clogged with wound exudate.

Figure 7:
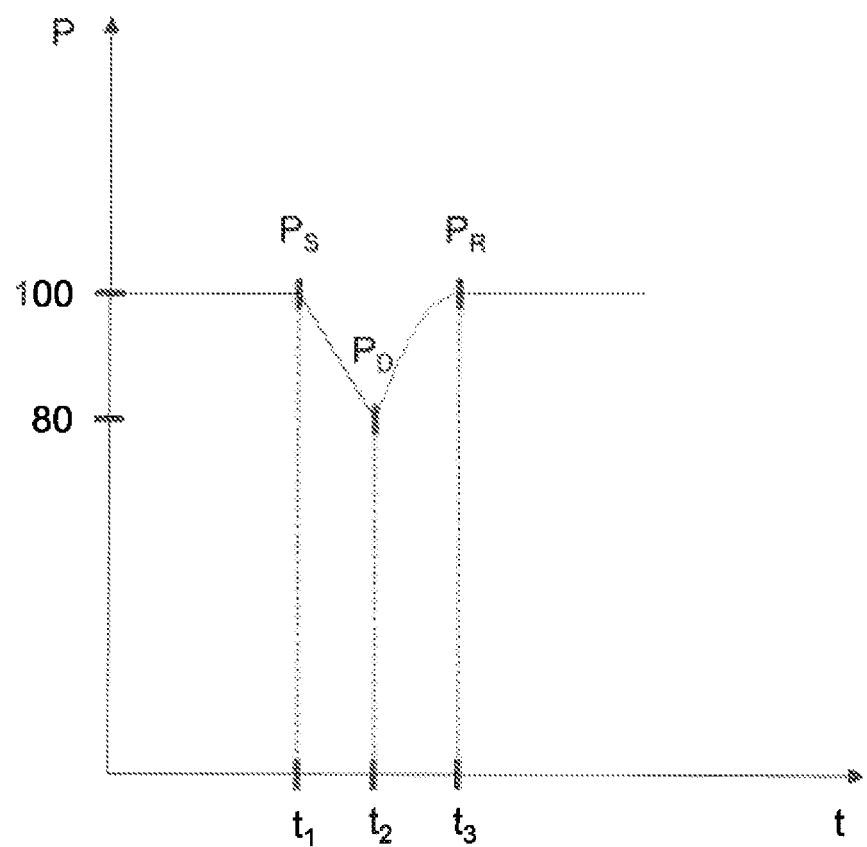

FIG. 7 shows an example of the negative pressure curve in a npwt system during the blockage detection method (schematic representation). The x-axis represents time (t), the y-axis represents negative pressure (P). In this example, the npwt system generates a stable negative pressure $P_S$ of 100 mmHg. The stability of the negative pressure is schematically indicated in FIG. 7 by the straight pressure curve (parallel to the x-axis) prior to time $t_1$. At time $t_1$, the ventilation step is initiated by opening the relief valve and at the same time stopping the pump of the npwt system. By opening the valve, air enters into the fluid path leading to a negative pressure decrease such that the pressure curve in FIG. 7 declines. After a pressure drop of 20% (that is when the negative pressure is at 80 mmHg ($P_D$)), the relief valve closes. Closure of the relief valve occurs at time $t_2$. Subsequently, the npwt system re-establishes the negative pressure, which was present at the beginning of the ventilation step (i.e. 100 mmHg in this example). Therefore, the pressure increases between $t_2$ and $t_3$. Starting with time $t_3$ the npwt system is on a negative pressure level of 100 mmHg. $P_R$ in FIG. 7 stands for the negative pressure at time $t_3$. Pressure $P_R$ is equal to (corresponds to) pressure $P_S$. Any first or any second blockage detection data set in this example is derived from the parameters $P_S$, $P_D$, the pressure gradient (between $t_1$ and $t_2$) and the number of pump turns (between $t_2$ and $t_3$).

The method for determining a blockage condition in a negative pressure wound therapy system during a negative pressure wound therapy disclosed herein includes a classification algorithm. In principle, a classification algorithm is used to decide, if an individual event belongs to a first or to a second class of events. In order to establish a classification algorithm a high number of experiments ("training experiments") has to be done to generate a plurality of events corresponding to one of the two classes (for example 50 experiments of events belonging to the first class and 50 experiments of events belonging to the second class). Furthermore, it is necessary to establish criteria which are used to discriminate the two classes. It is possible to represent the single events by entering each event into an n-dimensional data space. Each data point represents an individual event characterized by n parameters. If each of the two classes form an interconnected group of data (in the n-dimensional space), which does not overlap with the other class, it is possible to discriminate the groups by using a (n−1)-dimensional separator. The separator is also called hyperplane. If the data space is 3-dimensional, the hyperplane is a plane. If the data space is 2-dimensional, the hyperplane is a line. The hyperplane can be constructed "manually". Preferably, the hyperplane is established by using a support vector machine. FIGS. 8 *a* to *c* exemplary show training experiments required to establish a separation plane (hyperplane). Said hyperplane is used to perform a blockage detection method as described herein. In other words: The hyperplane is used as a blockage detection function.

FIGS. 8 *a* to *c* show the separation plane (blockage detection function) from different perspectives. The figures provide an example of a three-dimensional space (coordinate system) and a separation plane, which can be used for the blockage detection classification algorithm. The x-axis of the diagrams represents values derived ("transformed") from the number of pump turns (i.e. the number of pump turns were put in relation to the pressure drop ($P_S-P_D$)). The y-axis of the diagrams represents values derived ("transformed") from the pressure gradient (i.e. the pressure gradient was put in relation to $0.5 \times (P_S+P_D)$). Finally, the z-axis of the diagrams represents the start pressure. In this case the negative pressure values represented by the z-axis are provided with negative algebraic signs. The diagrams in FIGS. 8 *a* to *c* also show the blockage detection data sets that were generated as a result of a plurality of blockage detection training experiments. Each data point in the coordinate system corresponds to a blockage detection data set. The circles in the diagrams indicate first blockage detection data sets each representing an unblocked condition. The triangles in the diagrams indicate second blockage detection data sets each representing a blocked condition. As can be seen in the diagrams, the first and the second blockage detection data sets are forming classes which do not overlap with each other. It is possible to separate the first from the second class by a 2-dimensional plane. The calculation of the separation plane shown in FIGS. 8 *a* to *c* was done by using a standard support vector machine. The separation plane provides a measure whether any individual future blockage detection event (represented by a blockage detection data set), which is the result of performing the blockage detection method disclosed herein, corresponds to an unblocked condition (first class) or to a blocked condition (second class). All data points located above (to the right of) the separation plane are classified as an unblocked condition (first class) of the examined negative pressure wound therapy system. In contrast, all data points located underneath (to the left of) the separation plane are classified as a blocked condition (second class) of the examined negative pressure wound therapy system. In FIG. 8 *a*, two arrows indicate the direction of "above/to the right (a/r)" and "underneath/to the left (u/l)" in connection with the separation plane.

To generate the blockage detection data sets shown in FIGS. 8 *a* to *c*, a negative pressure wound therapy system as described in connection with FIG. 2 and FIG. 3 was experimentally subjected to a series of unblocked and to a series of blocked conditions. The experiments included the use of the wound simulator device basically as disclosed in the international application WO 2010/072349 A1 of the applicant. To generate negative pressure, the tested negative pressure wound therapy system used the membrane pump SP622 EC-BL of the company Schwarzer. Furthermore, the tested negative pressure wound therapy system executed the aforementioned pressure control method (first and second pressure control method) to control the pump. The negative pressure measurements for the start pressure and the pressure gradient as well as the number of pump turns (revolutions) according to the aforementioned blockage detection method were recorded during the experiments. Moreover, the blockage condition was determined during the experiments. In this way the experimentally determined data points could be assigned to either a blocked condition or to an unblocked condition.

FIGS. 8 *a* to *c* only provides an example for a blockage detection function (hyperplane), which was determined for a particular negative pressure wound therapy system. If the blockage detection method should be applied to another negative pressure wound therapy system, it may be necessary to repeat the experiments and to calculate a new blockage detection function.

Method of Determining a Canister Full Condition in a Negative Pressure Wound Therapy System (Canister Full Detection Method)

In principle, detection of a canister full status (blocked canister port/filter) is based on monitoring the pressure at the pump and pump speed over time. It is preferred that the canister full detection method runs continuously while negative pressure wound therapy is active. The canister full detection method is in particular designated for an npwt system comprising a moisture sensitive filter in the fluid path between the canister and the pressure sensor (such as the npwt system described in FIG. 3). The canister full detection method works independently of the tube blockage detection method. The canister full detection method suggested in the present specification is robust and works precisely and reliably. Moreover, the disclosed method is easy to perform once the classification algorithm has been established.

Similar to the blockage detection method explained previously, the canister full detection method uses a classification algorithm to discriminate a "canister full" from a "canister not full" condition. The canister full detection method evaluates a score based on two variables. Said variables are derived from the most recent 3 seconds of pump speed history and pressure sensor data point history:

1) The number of pump turns (revolutions) in the last 3 seconds.

2) A pressure variation score which represents the degree to which the pressure has both increased and decreased over the last 3 seconds, derived from the product of pressure increments and decrements over the period.

Preferably, the canister full detection method does not initiate until sufficient information is available so that significant results can be expected. Accordingly, the recorded data are first checked to determine if there is sufficient information to correctly evaluate whether the canister is full or not. For example, if the pump has not turned a single revolution, then the data do not comprise sufficient information. In such a situation the algorithm will bypass evaluation until the conditions for a significant evaluation are met.

Figure 9:
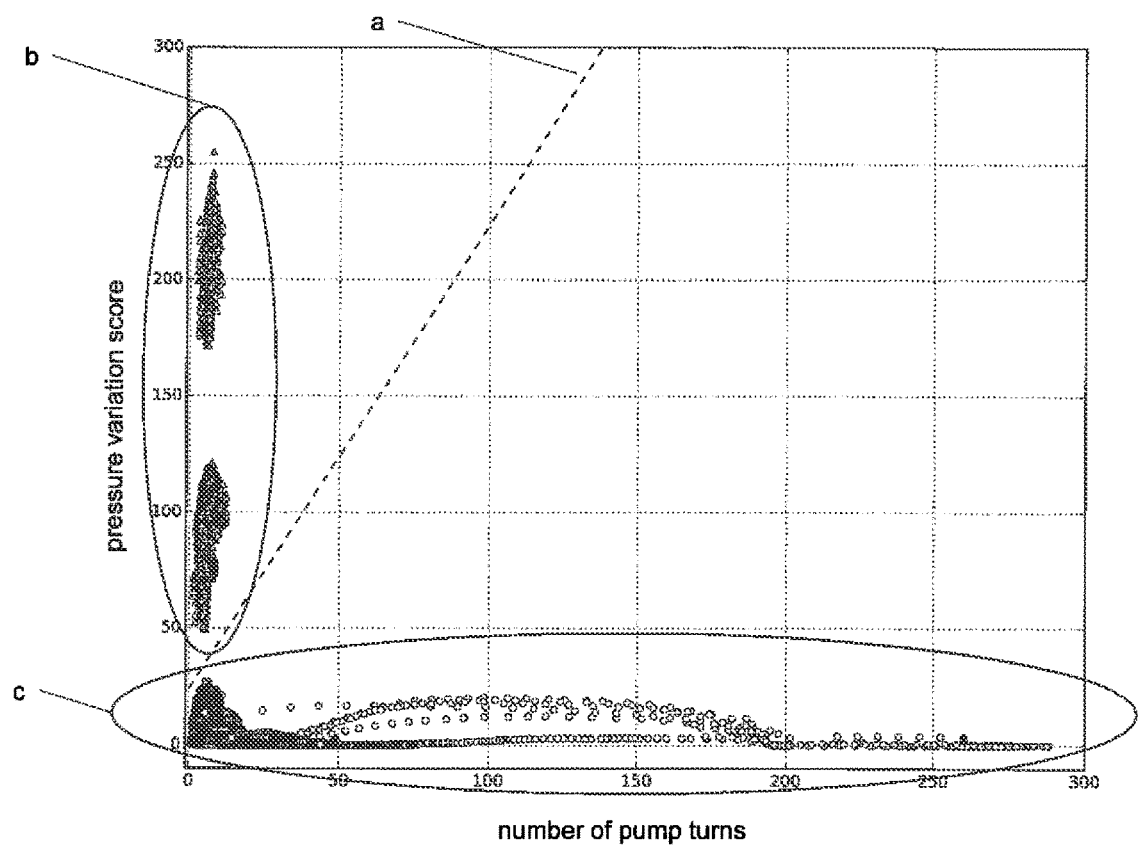

The canister full detection method is evaluated using a linear function which describes a line in 2D space that separates blocked points from unblocked points according to the graph exemplarily depicted in FIG. 9. If the evaluation results in a detection of a canister full condition, an alarm may be generated by the negative pressure wound therapy system to notify the user accordingly. The user may then replace the full canister by a new one and continue the negative pressure wound therapy.

FIG. 9 shows an example of a canister full detection function (separation line or "hyperplane"; dotted straight line with reference sign "a" in the diagram) in a two-dimensional space (coordinate system). The separation line is required to perform the classification algorithm included in the canister full detection method according to aspects or preferred embodiments of the invention. The x-axis of the diagram represents the number of pump turns (revolutions). The y-axis of the diagram represents the pressure variation score. The diagram in FIG. 9 also shows experimentally determined canister full detection data sets (as data points in the coordinate system) that were used for calculating the separation line. The circles in the diagram indicate data sets representing a canister not full condition (encircled by line "c"). The entirety of circles forms the first class of events each corresponding to a canister not full condition. The triangles in the diagram indicate data sets representing a canister full condition (encircled by line "b"). Accordingly, the entirety of triangles forms the second class of events, each corresponding to a canister full condition. As can be seen in the diagram, the first and the second class of canister full detection data sets do not overlap with each other. The calculation of the separation line includes the use of a standard support vector machine. The separation line provides a measure whether any individual future canister detection event (represented by a canister full detection data set), which is the result of performing the canister detection method disclosed herein, corresponds to a canister not full condition (first class) or to a canister full condition (second class). All data points located above the separation line are classified as a canister full status (second class) of the examined negative pressure wound therapy system. In contrast, all data points located underneath the separation line are classified as a canister not full status (first class) of the examined negative pressure wound therapy system. For example, if in the course of the canister full detection method 10 revolutions and a pressure variation score of 100 mmHg are recorded, the corresponding data point would be located above the separation line. Accordingly, a canister full status would be recognised. If in the course of the canister full detection method 10 revolutions and a pressure variation score of only 20 mmHg are recorded, the corresponding data point would be located underneath the separation line. Thus, in this further example a canister not full status is determined.

To generate the data sets shown in FIG. 9, a negative pressure wound therapy system as described in connection with FIG. 2 and FIG. 3 was experimentally subjected to a series of canister full and to a series of canister not full conditions (the canister not full conditions included only partially filled canisters as well). The experiments included the use of the wound simulator device basically as disclosed in the international application WO 2010/072349 A1 of the applicant. To generate negative pressure, the tested negative pressure wound therapy system used the membrane pump SP622 EC-BL of the company Schwarzer. Furthermore, the tested negative pressure wound therapy system executed the aforementioned pressure control method (first and second pressure control method) to control the pump. The number of pump turns (revolutions) and the negative pressure measurements to calculate the pressure variation score according to the aforementioned canister full detection method were recorded during the experiments. Moreover, the filling degree of the canister was determined during the experiments. In this way the experimentally determined data points could be assigned to either a canister full status or to a canister not full status.

As already pointed out, FIG. 9 only provides an example for a canister full detection function, which was determined for a particular negative pressure wound therapy system. If the canister full detection method is used for other negative pressure wound therapy systems, it may be necessary to perform training experiments and to calculate a canister full detection function.

Method of Determining a Leakage Condition of a Negative Pressure Wound Therapy System (Leakage Detection Method)

Figure 10:
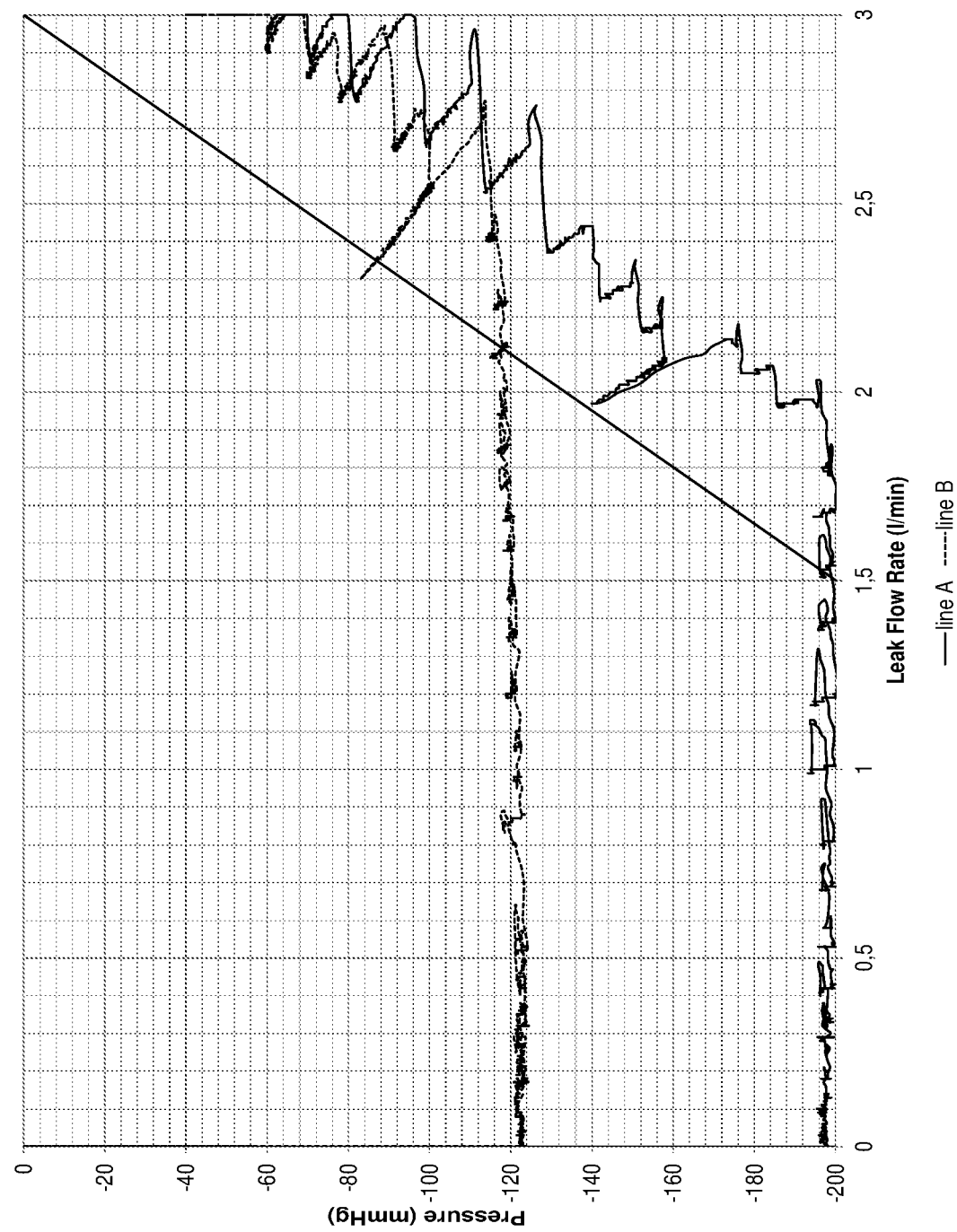

It is preferred that the leakage detection method is applied continuously while negative pressure wound therapy is active. The leakage detection method does not make use of the output value from the flow rate estimation. The leakage alarm is generated if the pump speed exceeds a predetermined value (threshold), for example 3000 RPM as shown in the diagram included in FIG. 10. This means that the red/green threshold (red=leakage condition; green=no leakage condition) is at a constant pump speed. In FIG. 10, said threshold is represented by the diagonal line. Consequently, the leak flow rate which causes a red status (leakage condition) will be higher as the target pressure decreases. This method has the benefit that it keeps the wound pressure close to the target pressure for as long as possible. Keeping the wound pressure close to the target pressure for as long as possible is achieved across the full pressure range. Also, the audio noise at the red/green threshold ("handover point") will be about the same for any target pressure. Having a more constant audio noise is more convenient for the patient. The leakage detection method as disclosed herein may be used in combination with the methods for controlling the speed of the suction pump as described previously (i.e. the first and the second pressure control method).

The results depicted in FIG. 10 were obtained by means of the following experiments: A negative pressure wound therapy system as previously described in connection with FIG. 2 and FIG. 3 including an artificial wound (size: 240 cm$^3$) is subjected to different leakage conditions. The experiments include the use of the wound simulator device as basically disclosed in the international application WO 2010/072349 A1 of the applicant. This wound simulator device comprises the aforementioned artificial wound. The wound simulator device comprises a valve and a flow meter to create and determine the leakage condition of the tested npwt system. To generate negative pressure, the tested negative pressure wound therapy system used the membrane pump SP622 EC-BL of the company Schwarzer. Furthermore, the tested negative pressure wound therapy system executes the aforementioned pressure control method (first and second pressure control method) to control the pump and to generate the desired target negative pressure value.

The amount of air entering the fluid path of the negative pressure wound therapy system is represented by the x-axis of the diagram in FIG. 10. The y-axis represents the negative pressure within the fluid path of the system. A higher leak flow rate corresponds to a higher leakage condition of the system. During the experiment, a target negative pressure value of approximately 200 mmHg is chosen (line A) and it is studied how long the negative pressure wound therapy system is able to maintain the desired target negative pressure value. The experiment is repeated with a target negative pressure value of approximately 125 mmHg (line B).

The inventors observed that the tested negative pressure wound therapy system is able to maintain the desired target negative pressure of 200 mmHg until the leak flow rate reaches a value of approximately 2 l/min (line A). Thus, any leak flow rates above approximately 2 l/min cannot be compensated by the pump contained in the negative pressure wound therapy system anymore. However, if the target negative pressure value is only 125 mmHg the negative pressure wound therapy system is able to compensate a higher leak flow rate, namely a leak flow rate up to approximately 2.5 l/min (line B). Consequently, the leak flow rate causing an alarm condition with regard to the negative pressure maintenance depends on the selected target negative pressure. The inventors unexpectedly found an advantageous and novel leakage detection method. Said method comprises generating a leakage alarm, if the pump speed exceeds a predetermined value. The methods considers the observed dependency of the critical leak flow rate and the target negative pressure. The diagonal line in FIG. 10 indicates when the pump runs with a constant speed of 3000 RPM. As can be seen in the diagram, an alarm is triggered (for example) at a leak flow rate of 1.5 l/min when the target negative pressure is 200 mmHg (line A). As further can be seen in the diagram, an alarm is triggered at a higher leak flow rate of approximately 2.1 l/min when the target negative pressure is 125 mmHg (line B). However, in both cases the negative pressure wound therapy system is still able to maintain the desired target negative pressure when the alarm is triggered. The same or a similar safety distance to the critical leak flow rate is provided. In principle, it may even be possible for the negative pressure wound therapy system of FIG. 10 to choose a higher pump speed for the leakage detection method since the safety distance to the critical leak flow rates could be further reduced. In general, the pump speed threshold will essentially depend on the type of the suction pump used (i.e. size and performance of pump).

Method of Estimating a Flow Rate of a Negative Pressure Wound Therapy System (Flow Rate Estimation Method)

It is preferred that the flow rate estimation is calculated continuously while negative pressure wound therapy is active. The flow rate is estimated as a function of pump speed and pump current. Pump pressure is not used to estimate flow rate. It was surprisingly found by the inventors that combining pump speed and pump current provides a better estimate of flow rate than pump speed alone (see FIGS. 11 *a* to *c*). For the flow rate estimation method, the speed of the suction pump can be controlled for example by means of the aforementioned pressure control method (first and second pressure control method).

Figure 11A:
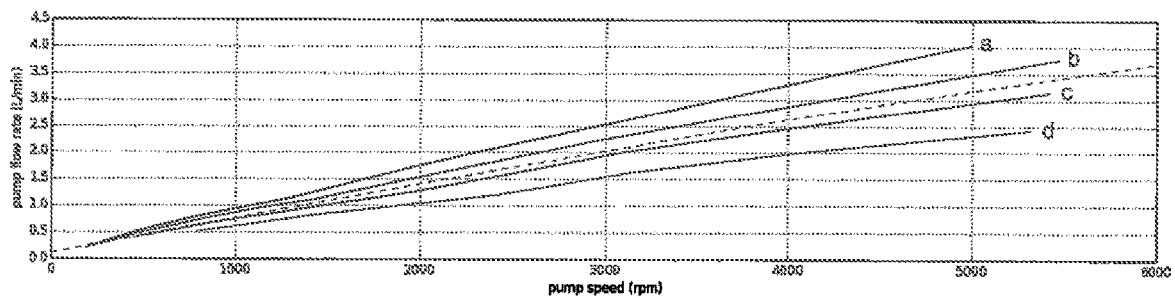
Figure 11B:
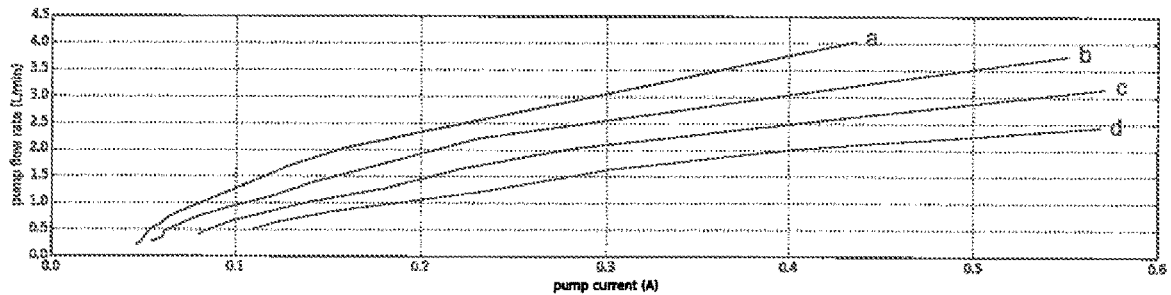
Figure 11C:
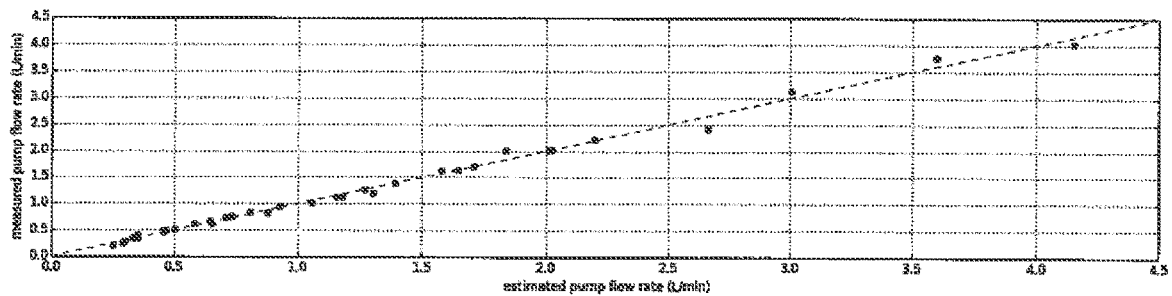

A negative pressure wound therapy system as previously described in connection with FIG. 2 and FIG. 3 including an artificial wound is subjected to different operating conditions (pressure, pump speed and leak flow rate). The results of the experiments are shown in FIGS. 11 *a* to *c*. The experiments include use of the wound simulator device as basically disclosed in the international application WO 2010/072349 A1 of the applicant. This wound simulator device comprises the aforementioned artificial wound. To generate negative pressure, the tested negative pressure wound therapy system uses the membrane pump SP622 EC-BL of the company Schwarzer. Furthermore, the tested negative pressure wound therapy system executes the aforementioned pressure control method (first and second pressure control method) to control the pump and to generate the desired target negative pressure values.

FIG. 11 *a* shows the graph of pump flow rate (as measured by an additional flow rate sensor located on the pump's exhaust) vs. the pump speed (as measured by the pump's tachometer). The four lines A to D show how the pump flow rate is broadly linearly related to the pump speed at constant pressure (constant negative pressure: line A=20 mmHg; line B=65 mmHg; line C=125 mmHg; line D=200 mmHg). However, the disparity/spread between the lines of constant pressure means that if just the pump speed is used to estimate flow rate (using a best fit polynomial estimator, shown as dotted line in FIG. 11 *a*), then the worst case estimation errors are: 0.86 l/min absolute error and 37% relative error. During the experiments, the pump current was also measured. FIG. 11 *b* shows the corresponding graph of pump flow rate vs. pump current. The inventors observed that there is likewise a dependency on pressure, but the relationship between current and flow at constant pressure is non-linear (i.e. not a straight line). Finally, FIG. 11 *c* shows a linear regression based estimate of the flow rate vs. the measured pump flow rate. The worst case estimation errors are: 0.24 l/min absolute error; 22% relative error (including flow rates 0.5 l/min); 10% relative error (excluding flow rates 0.5 l/min). These estimation errors are significantly lower than the previously mentioned estimation errors of FIG. 11 *a* (where the flow rate is estimated based on the pump speed alone). In summary, the performed experiments clearly show that the flow rate can be estimated very well based on the variables pump speed and pump current. As known in the prior art, the flow rate is a useful measure in negative pressure wound therapy systems and can be used, for instance, in control methods to detect a blockage condition or a leakage condition.

The following formulas provide an example how the flow rate can be mathematically derived from the pump current and the pump speed according to the invention. DF stands for "density factor". The density factor relates to the density of the air being evacuated by the npwt system. PC is the measured pump current. PS is the measured pump speed. Typically, PC and PS are measured at the same time. DFA stands for "density factor adjustment" and provides a mathematically modified density factor (DF) value. Finally, EFR represents the "estimated flow rate". The units of pump current and pump speed are Ampere (A) and revolutions per minute (RPM), respectively.

$$DF = \frac{PC + 0.0666}{\left(\frac{PS}{6000} + 0.826\right)^2} \quad 1)$$

$$DFA = 0.5 + \frac{1.5}{1 + e^{((DF \times 48.4) - 8.62)}} \quad 2)$$

$$EFR = \frac{PS}{2000} \times DFA \quad 3)$$

Wound Simulator Device/Experimental Setup

The inventors used a negative pressure wound simulator device to develop the control methods disclosed in the present specification. Such wound simulators are well-known. The general setup of the experiments has been described above. This paragraph provides supplemental information about the wound simulator and the experiments.

The inventors built a wound simulator basically in accordance with the wound simulator disclosed in WO 2010/072349 A1. The wound simulator comprises a recess which serves as an artificial wound. The artificial wound is connected to a source of liquid. Thus, a liquid, for example a synthetic wound exudate solution, can be introduced into the artificial wound. The npwt system to be tested may then suck the synthetic wound exudate solution from the artificial wound. The wound simulator comprises several sensors including a pressure sensor located in the artificial wound. The signals of this pressure sensor show whether the desired target negative pressure in the wound space is established or not. Furthermore, the wound simulator comprises a flow meter in connection with a valve. The tested negative pressure wound therapy system may be subjected to different leakage conditions by (stepwise) opening the valve. The aforementioned flow meter quantifies the leakage condition.

The inventors used commercially available dressing materials to cover/fill the artificial wound. The dressing material included a porous polyurethane foam to fill the artificial wound (VivanoMed® Foam; Paul Hartmann, Heidenheim, Germany) and an adhesive film (Hydrofilm®; Paul Hartmann, Heidenheim, Germany) to seal the artificial wound. A multilumen conduit having a suction and a ventilation lumen as well as a connector (VivanoTec® Port; Paul Hartmann, Heidenheim, Germany) enabled fluid communication between the dressing and the tested negative pressure device. The tested negative pressure device had a general structure as described in connection with FIG. 2 and FIG. 3. In some experiments the tested negative pressure device included additional or other components, for example a flow rate sensor located on the exhaust of the pump to develop the flow rate estimation method. In some experiments the controller of the negative pressure device was supported or replaced by an external computer such as a laptop to simplify data recording and processing.

During the experiments the negative pressure wound therapy system was subjected to different operating conditions. The operating conditions were chosen according to the particular purpose of the experiments and included, for example, different target negative pressure values, different sizes of the artificial wound or different amounts of the synthetic wound exudate solution.

The leakage conditions were generated as explained previously (by introducing different amounts of air into the artificial wound space).

The blockage conditions were generated by repeatedly interrupting fluid flow on different positions of the suction tube (for example, at a position close to the artificial wound as well as at a position remote from the artificial wound). Interruption of fluid flow was done by bending the conduit or by using a clamp. In order to verify that a blockage is actually present a flow meter interposed in the fluid path was used. It was also possible to inspect the flow with the naked eye by using a coloured synthetic wound exudate solution.

Canister full conditions were simulated by introducing varying amounts of coloured synthetic wound exudate solution into the canister. When the liquid reached the lower edge of the filter the canister was shaken softly so as to wet the filter completely. A test condition was classified as a canister full condition as soon as the filter was wet completely.

Mode of Pressure Sampling/Filter Technologies

According to a preferred embodiment, the therapy software module (controller) for the negative pressure wound therapy system continuously samples pressure measurements from the pressure sensor at a rate of 100 samples per second. Preferably, permanent sampling of pressure measurements is continued throughout the therapy independent of any system conditions such as pump activity or relief valve status. Inter alia, the pressure measurement values are used for controlling negative pressure, for regulating air flushes, for detecting tube blockages and for detecting a canister full condition.

Preferably, the pressure values measured by the pressure sensor are filtered in order to compensate for pressure fluctuations (noise suppression). Noise suppression can be done using standard filter technology such as digital filters (numerical implementation) or analogue filters (electronic circuit). Similarly, the pump speed measurements and pump current measurements may also be filtered in order to compensate for fluctuations. In the present specification, any reference to a pressure value measured by a pressure sensor may therefore relate to a filtered pressure value. This also applies to variables derived from pressure measurements such as the pressure gradient, the pressure error, or the pressure gradient error. Similarly, any reference to a pump speed measurement or to a pump current measurement may therefore relate to a filtered pump speed or to a filtered pump current, respectively.

The invention claimed is:

1. A negative pressure wound therapy system, comprising:
   an electrical pump to generate negative pressure;
   a tachometer configured to determine a pump speed associated with the electrical pump;
   a first fluid path fluidly connectable to a wound site and to the electrical pump such that the wound site is subjected to a negative pressure via the electrical pump;
   a pressure sensor configured to determine a negative pressure value, wherein the pressure sensor is located in the first fluid path between the wound site and the electrical pump;
   an input device to adjust settings on the negative pressure wound therapy system;
   a controller configured to execute the following steps:
   (i) multiply the determined pump speed by a constant to obtain a modification value; and
   (ii) combine the modification value with the determined negative pressure value to obtain a modified negative pressure value, wherein the modified negative pressure value corresponds to an estimated negative pressure present at the wound site.

2. A negative pressure wound therapy system according to claim 1, wherein when the negative pressure wound therapy system is in an active state, the controller is further adapted to continuously or intermittently execute the steps (i) and (ii).

3. The negative pressure wound therapy system according to claim 1, wherein the constant is a value selected from the range of 0.0025 mmHg/RPM to 0.0225 mmHg/RPM.

4. The negative pressure wound therapy system according to claim 3, wherein the range is between of 0.00375 mmHg/RPM to 0.015 mmHg/RPM.

5. The negative pressure wound therapy system according to claim 4, wherein the value of the constant is 0.0075 mmHg/RPM.

6. The negative pressure wound therapy system according to claim 1, wherein the electrical pump is a membrane pump.

7. The negative pressure wound therapy system according to claim 1, wherein the input device is a touch screen.

8. The negative pressure wound therapy system according to claim 1, which further comprises a canister for collecting fluid from the wound site.

9. The negative pressure wound therapy system according to claim 1, which further comprises a relief valve for venting the negative pressure wound therapy system.

10. The negative pressure wound therapy system according to claim 9, which further comprises a second fluid path fluidly connectable to the wound site and the relief valve, wherein the first fluid path and the second fluid path are in fluid communication at the wound site.

* * * * *